(12) United States Patent
Ravot

(10) Patent No.: US 7,563,878 B2
(45) Date of Patent: Jul. 21, 2009

(54) BACTERIAL PHYTASES AND METHOD FOR PRODUCING SAME

(75) Inventor: Gilles Ravot, Nimes (FR)

(73) Assignee: Adisseo France S.A.S., Antony (FR)

( * ) Notice: Subject to any disclaimer, the term of this patent is extended or adjusted under 35 U.S.C. 154(b) by 469 days.

(21) Appl. No.: 10/415,702

(22) PCT Filed: Nov. 12, 2001

(86) PCT No.: PCT/FR01/03527

§ 371 (c)(1),
(2), (4) Date: Jun. 11, 2003

(87) PCT Pub. No.: WO02/38774

PCT Pub. Date: May 16, 2002

(65) Prior Publication Data

US 2004/0096850 A1    May 20, 2004

(30) Foreign Application Priority Data

Nov. 10, 2000  (FR) .................................. 00 14448

(51) Int. Cl.
*C07H 21/02* (2006.01)
*C07H 21/04* (2006.01)
*A61K 39/38* (2006.01)
*A61K 39/00* (2006.01)
*A61K 39/02* (2006.01)

(52) U.S. Cl. .................... 536/23.1; 536/23.4; 536/23.7; 424/184.1; 424/185.1; 424/234.1; 435/41; 435/69.1

(58) Field of Classification Search ................ 536/23.1, 536/24.1, 24.2, 24.32; 530/300, 324
See application file for complete search history.

(56) References Cited

U.S. PATENT DOCUMENTS 6,583,266 B1 * 6/2003 Smith et al. .................. 530/350

FOREIGN PATENT DOCUMENTS

EP    0 955 362 A1    11/1999
EP    0 960 934 A1    12/1999
WO    WO 99/48380    9/1999

OTHER PUBLICATIONS

Thomas E. Creighton, in his book, "Proteins: Structures and Molecular Properties, 1984", (pp. 314-315).*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second paragraph).*
Reilly et al., "Acid phosphate precursor", EBI Database Accession No. Q47936, XP0022055621, 1996.
Reilly et al., "Francisella tularensis acid phosphatatse (acpA) gene, complete cds.", J Biol Chem, vol. 271, pp. 973-10983, 1996.
Amano, XP002171298, Section Ch, Week 199519, 1995.
Pen et al., "Phytase-containing Transgenic Seeds as a Novel Feed Additive for Improved Phosphorus Utilization", Nature, vol. 11, No. 7, 1993.
Kishimoto et al, "Acidiphilium aminolytica, new species: An acidophilic chemoorganotrophic bacterium isolated from acidic mineral environment", vol. 27, No. 3, pp. 131-136, 1993.
Amano, XP002171299, Section Ch, Week 199541, 1995.
Dou et al., "Restriction Endonuclease *AfaI* from *Acidiphilium facilis*, a new isoschizomer of *Rsal*: purification and properties", *Biochimica et Biophysica Acta*, 1009 (1989), pp. 83-86.
Mroz et al., "Apparent Digestiblity and Retention of Nutrients Bound to Phytate Complexes as Influenced by Microbial Phytase And Feeding Regimen in Pigs", *J. Anim. Sci.*, (1994), 72: 126-132.
English-language translation of Japanese Office Action.

* cited by examiner

*Primary Examiner*—Robert Mondesi
*Assistant Examiner*—Vanessa L. Ford
(74) *Attorney, Agent, or Firm*—Oliff & Berridge, PLC

(57) ABSTRACT

The invention concerns novel bacterial phytases, and their respective production methods. More particularly, the invention concerns novel phytases derived from bacteria of genus *Acidocella*, and polynucleotides coding for said phytases. The invention also concerns vectors containing said polynucleotides, and transformed host organisms expressing said phytases in their tissues. The invention further concerns novel bacterial extracts comprising at least a phytase activity.

24 Claims, 6 Drawing Sheets

SEQUENCE LISTING

<160> NUMBER OF SEQ ID NOS: 11

<210> SEQ ID NO 1
<211> LENGTH: 1665
<212> TYPE: DNA
<213> ORGANISM: Acidocella sp.
<220> FEATURE:
<221> NAME/KEY: CDS
<222> LOCATION: (1)..(1662)

<400> SEQUENCE: 1

```
atg aat atc cgc cgg gct ctt ttg tgc gcc tcc atg atg gtc tcg tcg      48
Met Asn Ile Arg Arg Ala Leu Leu Cys Ala Ser Met Met Val Ser Ser
1               5                   10                  15 atc acc ccc gcg gcg gcg cag acc gcc agc ctc ggc gcc acc gcg ccc      96
Ile Thr Pro Ala Ala Ala Gln Thr Ala Ser Leu Gly Ala Thr Ala Pro
            20                  25                  30 gcc tcc gcc agc gcc gca gct tcc tac acc gac gcg ctg ccg acc gcg     144
Ala Ser Ala Ser Ala Ala Ala Ser Tyr Thr Asp Ala Leu Pro Thr Ala
        35                  40                  45 acg ccg atc aag cat ctg gtc atc atc tat ggc gaa aac gtc tcc ttc     192
Thr Pro Ile Lys His Leu Val Ile Ile Tyr Gly Glu Asn Val Ser Phe
    50                  55                  60 gac cat tat ttc gcc acc tac ccg aag gcc acc aac ccg gcc ggt gag     240
Asp His Tyr Phe Ala Thr Tyr Pro Lys Ala Thr Asn Pro Ala Gly Glu
65                  70                  75                  80 ccg gcc ttc cat ggc agc ctg cat ggc cag aaa atc gat aac ctg gtc     288
Pro Ala Phe His Gly Ser Leu His Gly Gln Lys Ile Asp Asn Leu Val
                85                  90                  95 acc gcc aat ctg ctg agc aat aac ccg aac ttc acc aac gag aaa aac     336
Thr Ala Asn Leu Leu Ser Asn Asn Pro Asn Phe Thr Asn Glu Lys Asn
            100                 105                 110 ggc gcc ggg gcc gcc aac ccg ttc cgg ctg gac cgc acc cag gcc gcc     384
Gly Ala Gly Ala Ala Asn Pro Phe Arg Leu Asp Arg Thr Gln Ala Ala
        115                 120                 125 acc gcc gac cag aac cat gcc tac aag ccc gag cag gaa gcc tac gat     432
Thr Ala Asp Gln Asn His Ala Tyr Lys Pro Glu Gln Glu Ala Tyr Asp
    130                 135                 140 aac ggc aag atg gac ctg ttc ccc aaa tat acc ggc aag gcc agc gcc     480
Asn Gly Lys Met Asp Leu Phe Pro Lys Tyr Thr Gly Lys Ala Ser Ala
145                 150                 155                 160 ggc ggc gcc ggc gcc ttc ggc acc aag ggc cag gtg atg ggc tat ttc     528
Gly Gly Ala Gly Ala Phe Gly Thr Lys Gly Gln Val Met Gly Tyr Phe
                165                 170                 175 gac ggc aac acc gtc acc gcc ctc tgg aac tac gcc cag ggc tac gcg     576
Asp Gly Asn Thr Val Thr Ala Leu Trp Asn Tyr Ala Gln Gly Tyr Ala
            180                 185                 190 atg agc gac aat gcc tgg acc gac acc tac ggc ccc tcc acc ccc ggc     624
Met Ser Asp Asn Ala Trp Thr Asp Thr Tyr Gly Pro Ser Thr Pro Gly
        195                 200                 205
```

-continued

| | | |
|---|---|---|
| gcg ctg gcg gtg gtc tcc ggc cag acc aac ggc gcc gtg ccg gtg ctc<br>Ala Leu Ala Val Val Ser Gly Gln Thr Asn Gly Ala Val Pro Val Leu<br>210                                215                                220 | 672 |
| ggc acc tcg ccc aac ctg aac ccg gac ggc cag ggc ggc ttc acc gat<br>Gly Thr Ser Pro Asn Leu Asn Pro Asp Gly Gln Gly Gly Phe Thr Asp<br>225                                230                                235                              240 | 720 |
| gac ggc gat atc gac ccc gcc tac gat gtc tgc tcc agc aag aag gtc<br>Asp Gly Asp Ile Asp Pro Ala Tyr Asp Val Cys Ser Ser Lys Lys Val<br>                           245                                250                              255 | 768 |
| acc ttc aag atg gag ggc cag aat atc ggc gat ctg ctg aac gcc aag<br>Thr Phe Lys Met Glu Gly Gln Asn Ile Gly Asp Leu Leu Asn Ala Lys<br>                        260                                265                              270 | 816 |
| aaa gtc acc tgg ggc ggt ttc atg ggt ggc ttc gat ctc ggc ctc acc<br>Lys Val Thr Trp Gly Gly Phe Met Gly Gly Phe Asp Leu Gly Leu Thr<br>         275                                280                                285 | 864 |
| aac ccc aac ggc acc acc ggc tgc aag cgc tcc agc ttc gcc acc gcg<br>Asn Pro Asn Gly Thr Thr Gly Cys Lys Arg Ser Ser Phe Ala Thr Ala<br>         290                                295                                300 | 912 |
| gtc gat gcc ccc acc gcc gac tat atc ccg cac cat aac tgg ttc cag<br>Val Asp Ala Pro Thr Ala Asp Tyr Ile Pro His His Asn Trp Phe Gln<br>305                                310                                315                              320 | 960 |
| tat tac gcc tcc acc gcc aac tac acc cat gcc cgc ccg gcg gcg ctg<br>Tyr Tyr Ala Ser Thr Ala Asn Tyr Thr His Ala Arg Pro Ala Ala Leu<br>                        325                                330                              335 | 1008 |
| gac gat atc ggc tac agc ttc gcg cca tcc ggc gcc gcc gat ccg gcc<br>Asp Asp Ile Gly Tyr Ser Phe Ala Pro Ser Gly Ala Ala Asp Pro Ala<br>                        340                                345                              350 | 1056 |
| aac cat gaa tat gat ctg aag gat ttc gag gcg gcg gtg agc aag ggt<br>Asn His Glu Tyr Asp Leu Lys Asp Phe Glu Ala Ala Val Ser Lys Gly<br>                        355                                360                              365 | 1104 |
| gtg tat ccg gcc gtc tcc tat ctg aag ctg atc gcg gcc cag gat gcc<br>Val Tyr Pro Ala Val Ser Tyr Leu Lys Leu Ile Ala Ala Gln Asp Ala<br>         370                                375                                380 | 1152 |
| cat gcc ggc tat tcc gac ccg ctg gac gag cag gaa ggc gtg gtc aag<br>His Ala Gly Tyr Ser Asp Pro Leu Asp Glu Gln Glu Gly Val Val Lys<br>385                                390                                395                              400 | 1200 |
| gtc atc aac ttc ctg atg cgg cag ccg gat tgg aag aac acc gcc atc<br>Val Ile Asn Phe Leu Met Arg Gln Pro Asp Trp Lys Asn Thr Ala Ile<br>                        405                                410                              415 | 1248 |
| atc atc acc tat gat gat tcc gat ggc tgg tac gat cat gcc ttc gtg<br>Ile Ile Thr Tyr Asp Asp Ser Asp Gly Trp Tyr Asp His Ala Phe Val<br>                        420                                425                              430 | 1296 |
| acc ccg acc acc tcc tcc ttc agc ccg atg gac gcg ctg aac ggc aag<br>Thr Pro Thr Thr Ser Ser Phe Ser Pro Met Asp Ala Leu Asn Gly Lys<br>                        435                                440                              445 | 1344 |
| ggg gtc tgc ggg gcc ggc acc gaa ccg atg ggc ctg gcc ggc aag ccg<br>Gly Val Cys Gly Ala Gly Thr Glu Pro Met Gly Leu Ala Gly Lys Pro<br>         450                                455                                460 | 1392 |
| gtg cac ggg ctc tgc ggc ccc ggc acg cgc atc ccc ttc atg gtg atc<br>Val His Gly Leu Cys Gly Pro Gly Thr Arg Ile Pro Phe Met Val Ile<br>465                                470                                475                              480 | 1440 |
| tcg ccc tac gcg aag aaa ggt ttc atc gcc cat acg ctg atc agc cag<br>Ser Pro Tyr Ala Lys Lys Gly Phe Ile Ala His Thr Leu Ile Ser Gln<br>                        485                                490                              495 | 1488 |
| gcg tcg gtg gtg aaa ttc atc gcg gat aac tgg ctg ggc ggt gcc cgc<br>Ala Ser Val Val Lys Phe Ile Ala Asp Asn Trp Leu Gly Gly Ala Arg<br>                        500                                505                              510 | 1536 |
| ctg ggc ggc ggc tcc ttc gat gcc aat gcc ggc tcg atc atg gat atg<br>Leu Gly Gly Gly Ser Phe Asp Ala Asn Ala Gly Ser Ile Met Asp Met<br>         515                                520                                525 | 1584 |

```
ttc gat ttc aag acc gcg ccg aag ggc cgt gat gtg atg ctg ctg gat    1632
Phe Asp Phe Lys Thr Ala Pro Lys Gly Arg Asp Val Met Leu Leu Asp
    530                 535                 540 gcc gat acc ggc acc gcc gcg cac gcc gaa taa                        1665
Ala Asp Thr Gly Thr Ala Ala His Ala Glu
545                 550

<210> SEQ ID NO 2
<211> LENGTH: 554
<212> TYPE: PRT
<213> ORGANISM: Acidocella sp.

<400> SEQUENCE: 2

Met Asn Ile Arg Arg Ala Leu Leu Cys Ala Ser Met Met Val Ser Ser
1               5                   10                  15

Ile Thr Pro Ala Ala Gln Thr Ala Ser Leu Gly Ala Thr Ala Pro
            20                  25                  30

Ala Ser Ala Ser Ala Ala Ser Tyr Thr Asp Ala Leu Pro Thr Ala
        35                  40                  45

Thr Pro Ile Lys His Leu Val Ile Tyr Gly Glu Asn Val Ser Phe
    50                  55                  60

Asp His Tyr Phe Ala Thr Tyr Pro Lys Ala Thr Asn Pro Ala Gly Glu
65                  70                  75                  80

Pro Ala Phe His Gly Ser Leu His Gly Gln Lys Ile Asp Asn Leu Val
                85                  90                  95

Thr Ala Asn Leu Leu Ser Asn Asn Pro Asn Phe Thr Asn Glu Lys Asn
            100                 105                 110

Gly Ala Gly Ala Ala Asn Pro Phe Arg Leu Asp Arg Thr Gln Ala Ala
        115                 120                 125

Thr Ala Asp Gln Asn His Ala Tyr Lys Pro Glu Gln Glu Ala Tyr Asp
130                 135                 140

Asn Gly Lys Met Asp Leu Phe Pro Lys Tyr Thr Gly Lys Ala Ser Ala
145                 150                 155                 160

Gly Gly Ala Gly Ala Phe Gly Thr Lys Gly Gln Val Met Gly Tyr Phe
                165                 170                 175

Asp Gly Asn Thr Val Thr Ala Leu Trp Asn Tyr Ala Gln Gly Tyr Ala
            180                 185                 190

Met Ser Asp Asn Ala Trp Thr Asp Thr Tyr Gly Pro Ser Thr Pro Gly
        195                 200                 205

Ala Leu Ala Val Val Ser Gly Gln Thr Asn Gly Ala Val Pro Val Leu
    210                 215                 220

Gly Thr Ser Pro Asn Leu Asn Pro Asp Gly Gln Gly Phe Thr Asp
225                 230                 235                 240

Asp Gly Asp Ile Asp Pro Ala Tyr Asp Val Cys Ser Ser Lys Lys Val
                245                 250                 255

Thr Phe Lys Met Glu Gly Gln Asn Ile Gly Asp Leu Leu Asn Ala Lys
            260                 265                 270

Lys Val Thr Trp Gly Gly Phe Met Gly Gly Phe Asp Leu Gly Leu Thr
        275                 280                 285

Asn Pro Asn Gly Thr Thr Gly Cys Lys Arg Ser Ser Phe Ala Thr Ala
    290                 295                 300

Val Asp Ala Pro Thr Ala Asp Tyr Ile Pro His His Asn Trp Phe Gln
305                 310                 315                 320

Tyr Tyr Ala Ser Thr Ala Asn Tyr Thr His Ala Arg Pro Ala Ala Leu
                325                 330                 335
```

Asp Asp Ile Gly Tyr Ser Phe Ala Pro Ser Gly Ala Ala Asp Pro Ala
                340                 345                 350

Asn His Glu Tyr Asp Leu Lys Asp Phe Glu Ala Ala Val Ser Lys Gly
            355                 360                 365

Val Tyr Pro Ala Val Ser Tyr Leu Lys Leu Ile Ala Ala Gln Asp Ala
        370                 375                 380

His Ala Gly Tyr Ser Asp Pro Leu Asp Glu Gln Glu Gly Val Val Lys
385                 390                 395                 400

Val Ile Asn Phe Leu Met Arg Gln Pro Asp Trp Lys Asn Thr Ala Ile
                405                 410                 415

Ile Ile Thr Tyr Asp Asp Ser Asp Gly Trp Tyr Asp His Ala Phe Val
            420                 425                 430

Thr Pro Thr Thr Ser Ser Phe Ser Pro Met Asp Ala Leu Asn Gly Lys
        435                 440                 445

Gly Val Cys Gly Ala Gly Thr Glu Pro Met Gly Leu Ala Gly Lys Pro
    450                 455                 460

Val His Gly Leu Cys Gly Pro Gly Thr Arg Ile Pro Phe Met Val Ile
465                 470                 475                 480

Ser Pro Tyr Ala Lys Lys Gly Phe Ile Ala His Thr Leu Ile Ser Gln
                485                 490                 495

Ala Ser Val Val Lys Phe Ile Ala Asp Asn Trp Leu Gly Gly Ala Arg
            500                 505                 510

Leu Gly Gly Gly Ser Phe Asp Ala Asn Ala Gly Ser Ile Met Asp Met
        515                 520                 525

Phe Asp Phe Lys Thr Ala Pro Lys Gly Arg Asp Val Met Leu Leu Asp
    530                 535                 540

Ala Asp Thr Gly Thr Ala Ala His Ala Glu
545                 550

<210> SEQ ID NO 3
<211> LENGTH: 20
<212> TYPE: DNA
<213> ORGANISM: Artificial Sequence
<220> FEATURE:
<223> OTHER INFORMATION: Oligo10
<220> FEATURE:
<221> NAME/KEY: misc_feature
<222> LOCATION: (9)..(9)
<223> OTHER INFORMATION: n = a or g or c or t or other.
<220> FEATURE:
<221> NAME/KEY: misc_feature
<222> LOCATION: (12)..(12)
<223> OTHER INFORMATION: n = a or g or c or t or other.

<400> SEQUENCE: 3
atdatdatng cngtrttytt                                          20

<210> SEQ ID NO 4
<211> LENGTH: 32
<212> TYPE: DNA
<213> ORGANISM: Artificial Sequence
<220> FEATURE:
<223> OTHER INFORMATION: Oligo12

<400> SEQUENCE: 4
tcrtcrtasg tgatgatgat sgcsgtrtty tt                            32

<210> SEQ ID NO 5
<211> LENGTH: 23
<212> TYPE: DNA

```
<213> ORGANISM: Artificial Sequence
<220> FEATURE:
<223> OTHER INFORMATION: Oligo22
<220> FEATURE:
<221> NAME/KEY: misc_feature
<222> LOCATION: (12)..(12)
<223> OTHER INFORMATION: n = a or g or c or t or other.

<400> SEQUENCE: 5
aaratggarg gncaraayat hgg                                              23

<210> SEQ ID NO 6
<211> LENGTH: 23
<212> TYPE: DNA
<213> ORGANISM: Artificial Sequence
<220> FEATURE:
<223> OTHER INFORMATION: Oligo23

<400> SEQUENCE: 6
atggaaggcc agaayatcgg cga                                              23

<210> SEQ ID NO 7
<211> LENGTH: 23
<212> TYPE: DNA
<213> ORGANISM: Artificial Sequence
<220> FEATURE:
<223> OTHER INFORMATION: Oligo25

<400> SEQUENCE: 7
atcggcgayc tbctbaaygc caa                                              23

<210> SEQ ID NO 8
<211> LENGTH: 19
<212> TYPE: DNA
<213> ORGANISM: Artificial Sequence
<220> FEATURE:
<223> OTHER INFORMATION: Oligo29

<400> SEQUENCE: 8
ttcatgggtg gcttcgatc                                                   19

<210> SEQ ID NO 9
<211> LENGTH: 20
<212> TYPE: DNA
<213> ORGANISM: Artificial Sequence
<220> FEATURE:
<223> OTHER INFORMATION: Oligo30

<400> SEQUENCE: 9
gctgccgcat caggaagttg                                                  20

<210> SEQ ID NO 10
<211> LENGTH: 32
<212> TYPE: DNA
<213> ORGANISM: Artificial Sequence
<220> FEATURE:
<223> OTHER INFORMATION: 5'ORF281

<400> SEQUENCE: 10
taacgataac atatgaatat ccgccgggct ct                                    32

<210> SEQ ID NO 11
<211> LENGTH: 33
<212> TYPE: DNA
<213> ORGANISM: Artificial Sequence
<220> FEATURE:
<223> OTHER INFORMATION: 3'ORF281
```

```
<400> SEQUENCE: 11
atatctgata agctttattt cggcgtgcgc ggc                              33
```

BACTERIAL PHYTASES AND METHOD FOR PRODUCING SAME

The present invention relates to novel phytases of bacterial origin, and also to the respective methods for the production thereof. The present invention relates more particularly to novel phytases derived from bacteria of the *Acidocella* genus, and also to the polynucleotides encoding these phytases. The invention also relates to vectors containing these polynucleotides, and to transformed host organisms expressing said phytases in their tissues. The invention also relates to novel bacterial extracts comprising at least one phytase activity.

In particular, the bacterial extracts and the phytases of the present invention are particularly suitable for use in feed compositions intended for animal nutrition. This suitability is associated with their properties, in particular their activity under temperature and pH conditions corresponding to the conditions for preparing said compositions and also those encountered in the digestive system of animals.

Phosphorus is an element essential to the life of all organisms. In particular, it is of the utmost importance for farm animal breeders to be sure that their animals ingest a sufficient amount thereof to optimize their growth and development. Most farm animals are fed with plant-based feed compositions. These plants contain large amounts of phosphate which they store in their tissues in the form of a storage compound, phytic acid. On average, phytic acid contains 50 to 70% of the phosphorus present in plants. Phytic acid is naturally mobilized and the phosphate which it contains is released in most farm animals, in particular ruminants. However, phytic acid is not metabolized by monogastric animals such as pigs and poultry. In these animals, the phytic acid contained in their food intake is therefore discharged with the excrements, and the breeder has to supplement said intake with inorganic phosphate so that his animals ingest a sufficient amount of phosphorus. This strategy engenders additional expenditure for the breeder and generates pollution derived from the discharge into the environment of the non-assimilated phytic acid. This pollution is increased all the more in areas of intensive breeding.

Phytic acid is also known to be a chelator of important nutritive elements contained in the food intake, such as, for example, magnesium, calcium, zinc or iron. This property leads to a decrease in the nutritive quality of the food intake, giving phytic acid the property of an antinutritional agent.

In order to respond to the various drawbacks associated with the lack of assimilation of phytic acid by monogastric animals, the introduction of an enzyme, phytase, into the food intake of these livestock animals has been envisioned. Phytase hydrolyzes phytic acid, releasing inositol and inorganic phosphate. Phytases, and the genes encoding these phytases, have been isolated from many organisms. Phytases have mainly been isolated from fungi (Howson and Davis, 1983, Enzyme Microb. Technol. 5, 377-382; Wyss et al., 1999, Appl. Environ. Microbiol., 65(2), 359-366). Among the fungi which produce a phytase, mention may be made of fungi of the *Aspergillus* genus, in particular *A. ficuum* (Ullah and Gibson, 1987, Preparative Biochemistry 17(1), 63-91; Ullah and Dischinger, 1993, Biochem. Biophys. Res. Commun., 192(2), 747-753), *A. terreus* (Mitchell et al., 1997, Microbiology, 143 (Pt 1), 245252), *A. niger* (Dvorakova et al., 1997, Folia Microbiol (Praha), 42(4), 349-352), *A. fumigatus* (Pasamontes et al., 1997, Appl. Environ. Microbiol., 63(5), 1696-1700), of the *Penicillium* genus, in particular *P. caseicolum*, of the *Myceliophthora* genus, in particular *M. thermophila* (Mitchell et al., 1997, Microbiology, 143 (Pt 1), 245-252), of the *Talaromyces* genus, in particular *T. thermophilus*, of the *Neurospora* genus, in particular *N. crassa* and *N. sitophila*, of the *Thermomyces* genus, in particular *T. lanuginosus* (Berka et al., 1998, Appl. Environ. Microbiol. 64(11), 4423-4427), or of the *Monascus* genus, in particular *M. anka*. Phytases have also been found in bacteria. By way of example, mention may be made of bacteria of the *Bacillus* genus, in particular *B. subtilis* (Powar and Jagannathan, 1982, J. Bacteriol. 151(3), 102-1108; Shimizu, 1992, Biosci. Biotech. Biochem. 56(8), 1266-1269; Keruvo et al., 1998, Appl. Environ. Microbiol. 64(6), 2079-2085), *Pseudomonas* genus (Cosgrove, 1970, Austral. J. Biol. Sci. 23, 1207-1220), *Escherichia* genus, in particular *E. coli* (Golovan et al., 2000, Can. J. Microbiol. 46, 59-71), *Enterobacter* genus (Yoon et al., 1996, Enzyme and microbial. Technol.; 18, 449-454), or *Streptomyces* genus. Yeast phytases have also been isolated (Dvorakova, 1998, Folia Microbiol. 43(4), 323-338), such as those of the yeasts *Schwaniiomyces occidentalis* and *Saccharomyces cerevisiae*. Finally, phytases have been found in plants, in particular in soybean (Ullah and Gibson, 1988, Arch. Biochem. Biophys., 260(2), 514-20), in maize (Maugenest et al., 1997, Biochem J., 322 (Pt 2), 511-7); Maugenest et al., 1999, Plant Mol. Biol., 39(3), 503-14), or in Arabidopsis (Mullaney and Ullah, 1998, Biochem. Biophys. Res. Commun., 251(1), 252-5).

Properties which make it possible to characterize phytases include the Michaelis constant (Km) with respect to phytic acid, the optimum pH and the optimum temperature for activity, and also the stability of this activity at given pHs and temperatures. Data relating to the structure of phytases can also be used, such as the molecular weight (MW), the isoelectric point (pI) or the peptide sequence. For it to be possible to use them in animal nutrition, phytases must have properties compatible with the processing undergone by the feedstuffs intended for this nutrition. In particular, the activity of the phytases used must be maintained and, if possible, must be optimal under the conditions of temperature and pH of the processes for preparing these feedstuffs, and also those present in the digestive tract of the animals ingesting these feedstuffs. These constraints lead mainly to a search for phytases with activity which withstands high temperature conditions, such as those used in the processes for preparing the feed compositions, and which withstands acid pH conditions, such as those present in the digestive tract of livestock animals.

In order to satisfy these criteria, phytases have been sought in organisms, in particular microorganisms, which develop in environments in which the conditions of temperature and pH correspond to these criteria. This strategy has made it possible to isolate the phytases which withstand high temperatures, such as, for example, those described in patent applications WO 97/35016 or EP 0 684 313, but also of phytases which have a low Km, such as, for example, those described in patent application EP 0 960 934. Another strategy has consisted in artificially modifying the sequence of known phytases by site-directed mutagenesis in order to give it advantageous properties. This strategy has in particular been described in patent applications WO 99/48380, EP 0 897 985 and EP 0 897 010.

Only a few phytases which are active at a low optimal pH have been identified. Such phytases have in particular been identified in fungi, such as the phytase of *Penicillium caseicolum* described in patent application JP 7067635 and that of *Monascus anka* described in patent application WO 98/13480, but also in yeast, such as the phytase of *Schwaniiomyces occidentalis* described in patent application EP 699 762. However, to date, no bacterium has led to a phytase having a low optimum pH, in particular an optimum pH of less than 4, being isolated and identified.

DESCRIPTION

Figure 1:
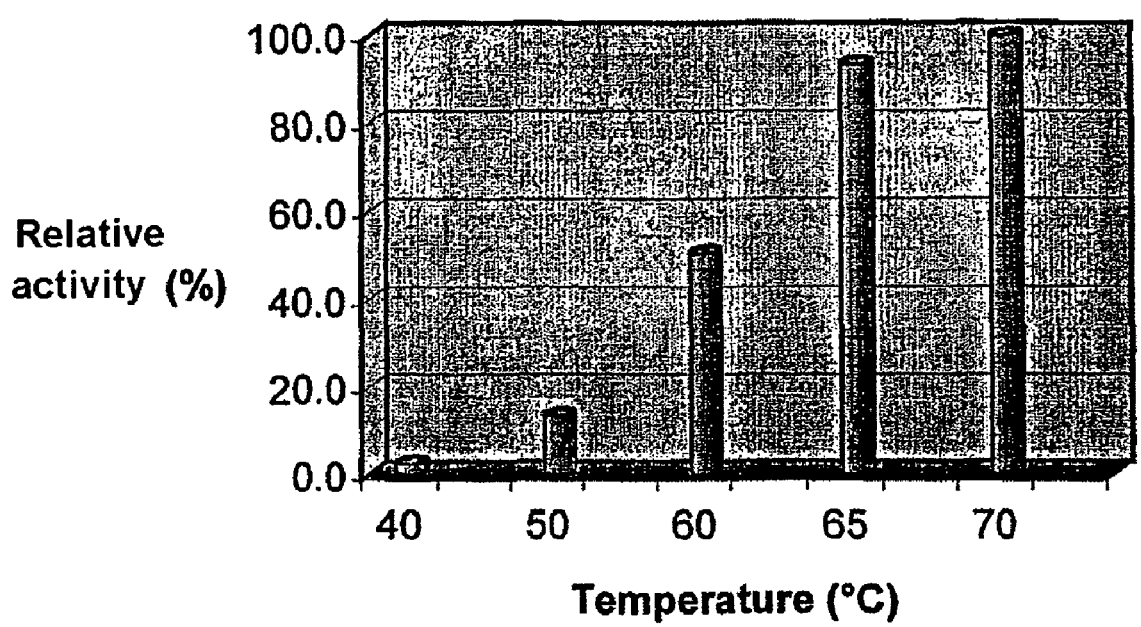
FIG. 1: Activity of the phytase of *Acidocella aminolytica* ATCC 51361 as a function of temperature. The value 100% of relative activity corresponds to the optimum activity of the phytase for a given temperature.

The present invention relates to isolated polynucleotides encoding a phytase described by the sequence identifier SEQ ID NO:2. This phytase and the polynucleotides which encode it are also characterized in that they originate from a bacterial strain of the *Acidocella* genus.

According to the present invention, the term "polynucleotide" is intended to mean a nucleic acid molecule composed of a natural or artificial sequence of bases which may be of the DNA or RNA type, preferably of the DNA type, in particular double-stranded. When said polynucleotide is natural, it is clearly understood that the invention does not cover this polynucleotide in its natural environment, but the same polynucleotide isolated and purified from the genome of the living organism in which it is naturally found. This polynucleotide may be obtained directly, by extraction and purification, or indirectly by copying. However, the present invention comprises said polynucleotide when it is integrated artificially into the genome of a living organism other than that in which it naturally exists, or when it is artificially reintroduced into the living organism from which it originates, as one or more copies in the genome of this organism. When this polynucleotide is a probe, it is generally single-stranded.

The invention therefore comprises the polynucleotides encoding the peptide sequence of the phytase described by the sequence identifier SEQ ID NO: 2. It is well known to those skilled in the art that this definition includes all polynucleotides which, although comprising nucleotide sequences which are different as a result of the degeneracy of the genetic code, encode the same amino acid sequence, and therefore the same phytase, that is represented by the sequence identifier SEQ ID NO: 2.

The present invention also comprises polynucleotides homologous to the polynucleotides described above, said homologous polynucleotides encoding phytases homologous to the phytase represented by the sequence identifier SEQ ID NO: 2. According to the invention, the term "homologous" is intended to mean polynucleotides encoding phytases, the sequences of which polynucleotides have modifications relative to the polynucleotides encoding the phytase represented by the sequence identifier SEQ ID NO: 2. The homologous polynucleotides are characterized by a degree of identity with the polynucleotides encoding the phytase represented by the sequence identifier SEQ ID NO: 2. The degree of identity between two homologous polynucleotides is obtained by comparing their sequences, and is generally expressed by a percentage of nucleotides which are identical between these sequences. This degree of identity is measured over a given sequence length, the shorter of the sequences compared determining the length of sequence over which the degree of identity of the homologous sequences is measured. The invention therefore covers polynucleotides having one or more sequence modifications relative to the polynucleotides encoding the phytase represented by the sequence identifier SEQ ID NO: 2, and encoding phytases the properties of which are equivalent to those of the phytase described by the sequence identifier SEQ ID NO: 2.

According to the invention, the expression "equivalent phytases" or "phytases with equivalent properties" is essentially intended to mean proteins having phytase activity, independently of their intrinsic properties such as the Km, the optimum pH for activity or the optimum temperature for activity. The level of phytase activity may be measured by any method for characterizing phytase activity. The term "phytase" is intended to mean an enzyme the catalytic activity of which consists in hydrolyzing phytic acid so as to release inositol and inorganic phosphate. However, since most phytases do not perform a complete hydrolysis of phytic acid (comprising 6 phosphates), the catalytic activity of a phytase according to the invention may lead to the release of inorganic phosphate and of myoinositol phosphate esters, said esters possibly being, depending on the hydrolytic capacity of the phytase, myoinositol mono-, di-, tri-, tetra- or pentaphosphate esters. By way of example, the phytase activity may be measured according to the method of Shimizu (1992, Biosci. Biotech. Biochem. 56(8), 1266-1269), in particular as described in Example 2. However, any method for characterizing a phytase activity, either by measuring the decrease in the amount of substrate or by measuring the accumulation of the products derived from the enzymatic reaction, may be used to measure the phytase activity. In particular, similar methods, using, for example, another substrate or other reagents, also make it possible to measure said phytase activity.

The sequence modifications present in the homologous polynucleotides may be additions, deletions or substitutions of nucleotides which may be natural or obtained by the usual mutagenesis techniques. It is known that such homologous polynucleotides, encoding proteins with equivalent functions, exist naturally in the genomes of different living species, and even in the genomes of different races, varieties or strains. Consequently, it is therefore easy for those skilled in the art, using the teaching of the polynucleotides encoding the peptide sequence represented by the sequence identifier SEQ ID NO: 2 according to the invention, to isolate such homologous polynucleotides using well-known techniques of molecular hybridization (Sambrook et al., 1989, Molecular Cloning: A Laboratory Manual, $2^{nd}$ edition, Nolan C. ed., New York: Cold Spring Harbor Laboratory Press).

Molecular hybridization is a pairing reaction which takes place between complementary strands of polynucleotides having a certain degree of identity between their nucleotide sequences. Hybridization therefore makes it possible, using the polynucleotides encoding the phytase represented by the sequence identifier SEQ ID NO: 2, to identify polynucleotides homologous to these polynucleotides, in the genome of living organisms other than the organism from which they are derived, for example other bacteria, in particular other strains of *Acidocella*, and encoding phytases with properties equivalent to the phytase represented by the sequence identifier SEQ ID No: 2. The greater the sequence identity between polynucleotides, the greater the possibility and ease of hybridization between said polynucleotides, and the greater the probability that these polynucleotides encode proteins with equivalent properties. The methods for hybridizing polynucleotides are widely described in the literature (Sambrook et al., 1989, Molecular Cloning: A Laboratory Manual, $2^{nd}$ Edition, Nolan C. ed., New York: Cold Spring Harbor Laboratory Press) and are well known to those skilled in the art. They are, for example, based on screening a genomic or cDNA library created from a living organism or from a tissue of this organism. The screening is carried out using a probe consisting of a known polynucleotide, or a fragment thereof, in order to identify, in these libraries, the polynucleotides homologous to said probe which will hybridize thereto. According to the invention, the probe consists of a polynucleotide encoding the phytase represented by the sequence identifier SEQ ID NO: 2, or a fragment thereof. In order to identify the polynucleotides to which the probe hybridizes, said probe is labeled, for example with radioactive elements, such as $^{32}P$ Commercially available nonradioactive labels which are well known to those skilled in the art may also be used.

The present invention therefore also comprises polynucleotides capable of hybridizing selectively to one of the polynucleotides encoding the phytase represented by the sequence identifier SEQ ID NO: 2, or a fragment thereof. It is understood that these polynucleotides are only part of the present invention if they encode a phytase equivalent to that represented by the sequence identifier SEQ ID NO: 2. According to the invention, the expression "polynucleotides capable of hybridizing selectively" is therefore intended to mean the polynucleotides which, by one of the usual methods of molecular hybridization, (Sambrook et al., 1989, Molecular Cloning: A Laboratory Manual, $2^{nd}$ edition, Nolan C. ed., New York: Cold Spring Harbor Laboratory Press), hybridize with a labeled probe consisting of one of the polynucleotides encoding the phytase represented by the sequence identifier SEQ ID NO: 2, or a fragment thereof, at a level greater than the nonspecific hybridization of said probe with other relatively nonhomologous polynucleotides, in particular other cDNAs if the polynucleotides probed are derived from a cDNA library. The level of hybridization is measured by virtue of the signal produced by the label of the probe. The level of the signal generated by the interaction between the polynucleotides capable of hybridizing selectively and the probe is generally 10 times, preferably 100 times, more intense than that generated by the interaction of the probe with the other polynucleotides generating a "background noise". The selective hybridization is generally obtained using normal, preferably stringent or very stringent, hybridization and washing conditions (for example hybridization with a buffer containing at least 5×SSC and 1% SDS at approximately 50° C.-60° C., and successive washes with 0.1% SDS and a gradual decrease in the concentration of SSC from 2×SSC to 0.4×SSC and also an increase in the temperature from 20° C. to 50° C.). Those skilled in the art will be able to adjust the hybridization conditions, i.e. essentially the temperature and the salt concentration of the buffers used for the hybridization step and the washing step. These conditions should in particular be adjusted as a function of the length of the probe used and of the degree of identity of the polynucleotides present in the library screened with this probe. It is necessary to adjust the hybridization conditions in order to optimize the signal generated by the homologous sequences which hybridize, while at the same time minimizing the background noise.

The polynucleotides capable of hybridizing selectively to the polynucleotides according to the invention may be isolated from genomic libraries or cDNA libraries produced, for example, from bacterial strains, in particular from strains of the *Acidocella* genus. The isolation of such polynucleotides may be carried out by standard hybridization techniques (Sambrook et al., 1989, Molecular Cloning: A Laboratory Manual, $2^{nd}$ edition, Nolan C. ed., New York: Cold Spring Harbor Laboratory Press), using, as a probe, a polynucleotide encoding the phytase represented by the sequence identifier SEQ ID NO: 2, a fragment of these polynucleotides, or a polynucleotide complementary thereto. When a polynucleotide has been isolated by these techniques, it is necessary to determine the sequence thereof and to identify the properties of the protein encoded by this polynucleotide, in particular to verify that this protein is a phytase equivalent to the phytase described by the sequence identifier SEQ ID NO: 2.

The hybridization techniques mentioned above therefore make it possible to isolate polynucleotides homologous to the polynucleotides encoding the phytase described by the sequence identifier SEQ ID NO: 2. Such polynucleotides, and the phytases which they encode, are readily identifiable by those skilled in the art in the biotechnology field who master standard molecular biology techniques. The invention therefore comprises polynucleotides homologous to the polynucleotides encoding the phytase described by the sequence identifier SEQ ID NO: 2. Advantageously, the degree of identity of the homologous polynucleotides will be at least 50% relative to the polynucleotides encoding the phytase represented by the sequence identifier SEQ ID NO: 2, preferably at least 70%, at least 80%, more preferentially at least 90%, and preferably at least 95%. The methods for measuring and identifying the degree of identity between sequences are well known to those skilled in the art. Use may be made, for example, of the programs PILEUP, BLAST (in particular Altschul et al., 1993, J. Mol. Evol. 36:290-300; Altschul et al., 1990, J. Mol. Biol. 215:403-10) or BestFit (Wisconsin Sequence Analysis Package, Version 8 for Unix, Genetics Computer Group, University Research Park, 575 Science Drive, Madison, Wis. 53711, using the algorithm of Smith and Waterman described in Applied Mathematics, 1981, No. 2, 482-489).

Such homologous polynucleotides may also be obtained artificially by conventional mutagenesis techniques.

A preferred polynucleotide encoding the phytase represented by the sequence identifier SEQ ID NO: 2 is represented by the sequence identifier SEQ ID NO: 1.

According to a particular embodiment of the invention, the polynucleotides encoding a phytase described above originate from a bacterium of the *Acidocella* genus.

Advantageously, the polynucleotides according to the invention encode a phytase for which the optimum pH activity is less than or equal to 4. The expression "optimum pH for activity" is intended to mean the pH value at which the activity of the phytase according to the invention is maximal, this activity being measured by the method mentioned above and corresponding to the amount of phytic acid degraded and of inorganic phosphate produced.

According to a particular embodiment of the invention, the polynucleotides according to the invention encode a phytase having the following properties:
(a) optimum temperature=65° C.
(b) optimum pH=3.5

According to another particular embodiment of the invention, the polynucleotides according to the invention encode a phytase having the following properties:
(a) optimum temperature=70° C.
(b) optimum pH=4

According to another particular embodiment of the invention, the polynucleotides according to the invention encode a phytase having the following properties:
(a) optimum temperature=60° C.
(b) optimum pH=3.5

Preferably, the polynucleotides according to the invention encode a phytase originating from a bacterial strain of the species *Acidocella aminolytica*, in particular the strain *A. aminolytica* ATCC 51361, or from a bacterial strain of the species *Acidocella facilis*, in particular the strain *A. facilis* ATCC 35904.

The present invention also relates to fragments of the polynucleotides described above. The term "fragment" in particular denotes a fragment of at least 20 nucleotides, in particular at least 50 nucleotides, and preferably at least 100 nucleotides. Such fragments are generally designated oligonucleotides. They may be used as hybridization probes to identify homologous polynucleotides, or as primers to identify and amplify such homologous polynucleotides by the PCR (Polymerase Chain Reaction) technique as described in Ausubel et al., (1987) Current Protocols in Molecular Biology, edit. John Wiley & Sons, Section 6.3-6.4.

The term "fragment" also denotes fragments of the polynucleotides according to the invention encoding a fragment of the phytase represented by the sequence identifier SEQ ID NO: 2, or a fragment of a phytase homologous or equivalent to the phytase represented by the sequence identifier SEQ ID NO: 2.

The present invention also relates to polynucleotides comprising at least one of the polynucleotides as described above.

All the polynucleotides described above encode either the phytase represented by the sequence identifier SEQ ID NO: 2, or a homologous phytase, or an active fragment of these phytases. Consequently, the invention therefore extends to all the phytases encoded by all of these polynucleotides. This definition therefore includes the phytase represented by the sequence identifier SEQ ID NO: 2, the phytases homologous to this phytase, and the active fragments of these phytases.

According to a preferred embodiment of the invention, the phytase is a protein comprising at least the peptide sequence described by the sequence identifier SEQ ID NO: 2. Preferably, the phytase represented by the peptide sequence described by the sequence identifier SEQ ID NO: 2 hydrolyzes 5 of the 6 phosphates present on a phytase molecule.

The invention therefore also comprises the phytases homologous to the phytase represented by the sequence identifier SEQ ID NO: 2. According to the invention, the term "homologous phytases" is intended to mean the phytases the sequences of which have modifications relative to the phytase represented by the sequence identifier SEQ ID NO: 2. Like the homologous polynucleotides, the homologous phytases are phytases the peptide sequences of which exhibit a certain degree of identity, which degree of identity is generally expressed by a percentage of identical amino acids. The invention therefore covers phytases which have one or more sequence modifications relative to the phytase represented by the sequence identifier SEQ ID NO: 2, and the properties of which are equivalent to those of the phytase described by the sequence identifier SEQ ID NO: 2. These modifications may be additions, deletions or substitutions of amino acids which may be natural or obtained by the usual mutagenesis techniques. Advantageously, the degree of identity of the homologous phytases will be at least 60% relative to the phytase represented by the sequence identifier SEQ ID NO: 2, preferably at least 70%, at least 80%, more preferentially at least 90%, and preferably at least 95%. The methods for measuring and identifying the degree of identity between the sequences are well known to those skilled in the art. Use may be made, for example, of the programs PILEUP, BLAST (in particular Altschul et al., 1993, J. Mol. Evol. 36:290-300; Altschul et al., 1990, J. Mol. Biol. 215:403-10) or BestFit (Wisconsin Sequence Analysis Package, Version 8 for Unix, Genetics Computer Group, University Research Park, 575 Science Drive, Madison, Wis. 53711, using the algorithm of Smith and Waterman described in Applied Mathematics, 1981, No. 2, 482-489).

According to a particular embodiment of the invention, the phytase according to the invention originates from a bacterium of the *Acidocella* genus.

Advantageously, the phytase according to the invention has an optimum pH for activity of less than or equal to 4. The expression "optimum pH for activity" is intended to mean the pH value at which the activity of the phytase according to the invention is maximal, this activity being measured by the method mentioned above and corresponding to the amount of phytic acid degraded and of inorganic phosphate produced.

According to a particular embodiment of the invention, the phytase has the following properties:
(a) optimum temperature=65° C.
(b) optimum pH=3.5

According to another particular embodiment of the invention, the phytase has the following properties:
(a) optimum temperature=70° C.
(b) optimum pH=4

According to another particular embodiment of the invention, the phytase has the following properties:
(a) optimum temperature=60° C.
(b) optimum pH=3.5

According to another particular embodiment of the invention, the phytase according to the invention originates from a bacterial strain of the species *Acidocella aminolytica*, in particular the strain *A. aminolytica* ATCC 51361, or from a bacterial strain of the species *Acidocella facilis*, in particular the strain *A. facilis* ATCC 35904.

The invention also extends to the fragments of the phytase represented by the sequence identifier SEQ ID NO: 2 and to the fragments of the homologous phytases. The term "fragment" is essentially intended to mean a biologically active fragment, i.e. a fragment having a phytase activity equivalent to that of the complete phytase, as measured by the assay described in example 2, or a similar assay.

The present invention also relates to a chimeric gene comprising, functionally linked to one another, at least one promoter which is functional in a host organism, a polynucleotide encoding a phytase according to the invention, and a terminator element that is functional in the same host organism. The various elements which a chimeric gene may contain are, firstly, elements regulating transcription, translation and maturation of proteins, such as a promoter, a sequence encoding a signal peptide or a transit peptide, or a terminator element constituting a polyadenylation signal and, secondly, a polynucleotide encoding a protein. The expression "functionally linked to one another" means that said elements of the chimeric gene are linked to one another in such a way that the function of one of these elements is affected by that of another. By way of example, a promoter is functionally linked to a coding sequence when it is capable of affecting the expression of said coding sequence. The construction of the chimeric gene according to the invention and the assembly of its various elements can be carried out using techniques well known to those skilled in the art, in particular those described in Sambrook et al. (1989, Molecular Cloning: A Laboratory Manual, Nolan C. ed., New York: Cold Spring Harbor Laboratory Press). The choice of the regulatory elements constituting the chimeric gene depends essentially on the host organism in which they must function, and those skilled in the art are capable of selecting regulatory elements which are functional in a given host organism. The term "functional" is intended to mean capable of functioning in a given host organism.

The promoters which the chimeric gene according to the invention may contain are either constitutive or inducible. By way of example, the promoters used for expression in bacteria may be chosen from the promoters mentioned below. For expression in *Escherichia coli* mention may be made of the lac, trp, lpp, phoA, recA, araBAD, proU, cst-1, tetA, cadA, nar, tac, trc, lpp-lac, Psyn, cspA, PL, PL-9G-50, PR-PL, T7, λPL-PT7, T3-lac, T5-lac, T4 gene 32, nprM-lac, VHb and the protein A promoters (Makrides, 1996, Microbiol. Rev. 60:512-538; Current Opinions in Biotechnology, 1996, 7; Weickert et al., 1996, Current Opinions in Biotechnology 7: 494-499) or else the $P_{trp}$ promoter (WO 99/64607). For expression in Gram-positive bacteria such as *Corynebacteria* or *Streptomyces*, mention may be made of the $P_{tipA}$ (Holmes et al., 1993, EMBO J. 12:3183-3191) or PS1 and PS2 (FR91/09870) promoters or those described in application EP0629699A2. For expression in yeasts and fungi, mention may be made of the *K. lactis* $P_{LAC4}$ promoters (Van den Berg et al., 1990, Bio/Technology 8:135-139) or the *K. lactis* $P_{pgk}$ promoter (patent application FR 91/05294), the *Trichoderma* tefl or cbhl promoter (WO 94/04673), the *Penicillium* his, csl or apf promoter (WO 00/68401) and the *Aspergillus* gla promoter (Gwynne et al., 1987, Bio/Technology 5:713-719).

The chimeric gene may also comprise a subcellular addressing sequence encoding a signal peptide or transit peptide. Such a sequence, located upstream or downstream of the polynucleotide encoding the phytase, makes it possible to direct said phytase specifically into a cellular compartment of the host organism, or to direct its secretion into the extracellular space. For example, the chimeric gene may comprise a sequence encoding a signal peptide or a transit peptide for directing the phytase toward a particular compartment of the cytoplasm, such as the mitochondria, the plasts, the endoplasmic reticulum or the vacuoles. Preferably, the addressing sequence encodes a signal peptide which addresses the phytase into the apoplast or the extracellular matrix.

According to one embodiment, the transit peptide may be a chloroplast, vacuolar or mitochondrial addressing signal which is then cleaved in the chloroplasts, the vacuoles or mitochondria. Such peptides are widely described in the literature: Neuhaus and Rodgers, 1998, Plant Molecular Biology 38: 127-144; EPSPS transit peptide described in patent U.S. Pat. No. 5,188,642; ribulose-biscarboxylase/oxygenase small subunit transit peptide (EP 189707).

According to another embodiment, the transit peptide may consist of a signal peptide for addressing into the bacterial periplasm, such as those of the pac (Schumacher et al., 1986, Nucl. Acids. Res. 14:5713-5727), ompA (Bowden and Georgiou, 1990, J. Biol. Chem. 265: 16761-16766) and phoA (Chang et al., 1986, Gene 44: 121-124) genes, or of a bacterial surface anchoring peptide, such as those of the PS1 and PS2 genes (FR91/09870).

The transit peptides may be single or double peptides. The double transit peptides are optionally separated by an intermediate sequence. By way of example of a chloroplast transit peptide, mention may be made of a double transit peptide comprising, in the direction of transcription, a sequence encoding a transit peptide of a plant gene encoding an enzyme located in plastids, a portion of sequence from the mature N-terminal portion of a plant gene encoding an enzyme located in plastids, and then a sequence encoding a second transit peptide of a plant gene encoding an enzyme located in plastids. Such double chloroplast transit peptides are, for example, described in patent application EP 0 508 909.

According to one embodiment, the transit peptide may be composed of various elements for increasing the amount of protein of interest secreted into the medium. Mention may thus be made of the combination of a carrier protein and a proteolytic cleavage site fused with the protein of interest (U.S. Pat. No. 6,130,063).

According to the invention, the chimeric gene may also comprise other regulatory sequences, which are located between the promoter and the coding sequence, such as transcription activators (enhancers).

The present invention also relates to a cloning and/or expression vector comprising a chimeric gene according to the invention. The vector according to the invention is of use for transforming a host organism and expressing in this organism a phytase. This vector may be a plasmid, a cosmid, a bacteriophage or a virus. Preferentially, the transformation vector according to the invention is a plasmid. Generally, the main qualities of this vector should be an ability to maintain itself and to self-replicate in the cells of the host organism, in particular by virtue of the presence of an origin of replication, and to express a phytase therein. For the purpose of stable transformation of a host organism, the vector may also integrate into the genome. The composition of the vector may then be limited to the elements required for synthesizing the phytase in the hosts. The choice of such a vector, and also the techniques of insertion of the chimeric gene according to the invention into this vector, are thoroughly described in Sambrook et al. (1989, Molecular Cloning: A Laboratory Manual, Nolan C. ed., New York: Cold Spring Harbor Laboratory Press) and are part of the general knowledge of those skilled in the art. Advantageously, the vector used in the present invention also contains, in addition to the chimeric gene according to the invention, a chimeric gene encoding a selectable marker. This selectable marker makes it possible to select the host organisms which are effectively transformed, i.e. those which incorporated the vector. According to a particular embodiment of the invention, the host organism to be transformed is a plant or a fungus. Among the selectable markers which can be used, mention may be made of markers containing genes for resistance to antibiotics or to fungicides, such as, for example, the hygromycin phosphotransferase gene (Gritz et al., 1983, Gene 25: 179-188; Punt et al., 1987; Gene 56: 117-24), that of streptothricin acetyltransferase, that encoding a polypeptide conferring phleomycin resistance, that of mutated beta-tubulin conferring benomyl resistance (Gold et al., 1994, Gene 142: 225-30), or that of bialaphos acetyltransferase (Avalos et al., 1989, Curr Genet, 16:369-72). Other markers may be genes to complement an auxotrophy, such as the pyrA, pyrB, pyrG, pyr4 (Buxton and Radford, 1983, Mol. Gen. Genet. 190:403-405), arg4, argB (Berse et al., 1983, Gene 25:109-117) and trpC (Goosen et al., 1989, Mol. Gen. Genet., 219:282-88) genes, the molybdopterin synthase gene (Appleyard et al., 1998, J Biol Chem 273: 14869-76; Unkles et al., 1999; J Biol Chem, 274:19286-93) or that of acetamidase (Beri and Turner, 1987, Curr Genet, 11:639-41). Another category of selectable markers consists of genes for tolerance to herbicides, such as the bar gene (White et al., NAR 18:1062, 1990) for bialaphos tolerance, the EPSPS gene (U.S. Pat. No. 5,188,642) for glyphosate tolerance, the HPPD gene (WO 96/38567) for isoxazole tolerance, or the glyphosate oxydoreductase gene (U.S. Pat. No. 5,463,175). Mention may also be made of genes encoding readily identifiable enzymes such as the GUS enzyme, or genes encoding pigments or enzymes regulating the production of pigments in the transformed cells. Such selectable marker genes are in particular described in patent applications WO 91/02071, WO 95/06128, WO 96/38567 and WO 97/04103.

The present invention also relates to transformed host organisms containing at least one chimeric gene according to the invention, either integrated into their genome or carried on an extrachromosomal genetic element, for example a plasmid. The term "host organism" is intended to mean any lower or higher monocellular or pluricellular organism into which the chimeric gene according to the invention may be introduced in order to produce a phytase according to the invention. Preferably, the host organism is a microorganism, in particular a fungus, for example of the *Penicillium, Aspergillus, Chrysosporium* or *Trichoderma* genus, a bacterium, for example of the *Escherichia* genus, in particular *E. coli*, of the *Corynebacterium* genus, or of the *Streptomyces* genus, a yeast, in particular of the Saccharomyces, *Kluyveromyces* or the *Pichia* genus, a baculovirus, or plant cells. The host organism may also be a plant or a part of a plant.

The expression "transformed host organism" is intended to mean a host organism which has incorporated into its genome, or in an extrachromosomal genetic element, for example a plasmid, at least one chimeric gene according to the invention, and consequently produces a phytase in its tissues, or in a culture medium. To obtain the host organisms according to the invention, those skilled in the art may use one of the many known transformation methods.

One of these methods consists in bringing the cells or tissues of the host organisms to be transformed into contact with polyethylene glycol (PEG) and with the vectors according to the invention (Chang and Cohen, 1979, Mol. Gen. Genet. 168(1), 111-115; Mercenier and Chassy, 1988, Biochimie 70(4), 503-517). Electroporation is another method, which consists in subjecting the cells or tissues to be transformed and the vectors of the invention to an electric field (Andreason and Evans, 1988, Biotechniques 6(7), 650-660; Shigekawa and Dower, 1989, Aust. J. Biotechnol. 3(1), 56-62). Another method consists in directly injecting the vectors into the cells or the tissues by microinjection (Gordon and Ruddle, 1985, Gene 33(2), 121-136). Advantageously, the "biolistic" method may be used. It consists in bombarding cells or tissues with particles onto which the vectors of the invention are adsorbed (Bruce et al., 1989, Proc. Natl. Acad. Sci. USA 86(24), 9692-9696; Klein et al., 1992, Biotechnology 10(3), 286-291; U.S. Pat. No. 4,945,050).

Several methods for transforming bacteria are described in the literature for *Escherichia coli* and other Gram-negative bacteria (Ausubel et al., 1995, Current Protocols in Molecular Biology, John Wiley and Sons, New York; Inoue et al., 1990, Gene 96: 23-28; Chung et al., 1989, Proc. Natl. Acad. Sci. USA 86: 2172-2175). Conjugation may also be used (Cameron et al., 1989, J. Bacteriol., 171: 547-557). For Grampositive bacteria, electroporation may be used, and also protoplast transformation, in particular for bacteria of the *Streptomyces* genus (Bonamy et al., 1990, FEMS Microbio. Lett 66: 263-270; Hopwood et al., 1985, Genetic Manipulation of *Streptomyces*: A Laboratory Manual. John Innes Foundation, Norwich).

Several methods for transforming fungi are also described in the literature (Talbot, 2001, Molecular and cellular biology of filamentous fungi, Oxford University Press, New York). Protoplast transformation with PEG is described for *Aspergillus* in EP 0260762, and an adaptation of this method to the species *Penicillium funiculosum* is described in WO 00/36120. Transformation by restriction enzyme mediated integration, or REMI (Sanchez et al., 1998, Mol. Gen. Genet. 258; 89-94), is also known, as is protoplast transformation using bacteria of the *Agrobacterium* genus (de Groot et al., 1998, Nature Biotechnology 16: 839-842). Techniques for transforming yeasts are also described in the literature, in particular in Ausubel et al. (1995, Current Protocols in Molecular Biology, John Wiley and Sons, New York) and Van den Berg et al. (1990, Bio/Technology 8: 135-139).

In the particular case when the host organism to be transformed is of plant origin, the plant cells or tissues may preferentially be transformed using bacteria of the *Agrobacterium* genus, preferably by infection of the cells or tissues of said plants with *A. tumefaciens* (Knopf, 1979, Subcell. Biochem. 6, 143173; Shaw et al., 1983, Gene 23(3):315-330) or *A. rhizogenes* (Bevan and Chilton, 1982, Annu. Rev. Genet. 16:357-384; Tepfer and Casse-Delbart, 1987, Microbiol. Sci. 4(1), 24-28). Preferentially, the transformation of plant cells or tissues with *Agrobacterium tumefaciens* is carried out according to the protocol described by Ishida et al. (1996, Nat. Biotechnol. 14 (6), 745-750). Those skilled in the art will choose the appropriate method depending on the nature of the host organisms to be transformed.

The present invention also relates to a novel bacterial extract comprising at least one phytase activity, characterized in that it originates from a bacterium of the *Acidocella* genus. According to the present invention, the term "bacterial extract" is intended to mean the fraction which is water-soluble or soluble in an aqueous solution, said fraction being derived from grinding bacteria and separating, by centrifugation, the bacterial constituents thus released into a solid fraction and a liquid fraction, the liquid fraction comprising all of the soluble bacterial constituents. The phytase activity corresponds to the amount of phytic acid degraded and is generally measured by quantification of the inorganic phosphate released by the enzyme reaction. In particular, the phytase activity is measured according to the method of Shimizu (1992, Biosci. Biotech. Biochem, 56(8), 1266-1269), in particular as described in Example 2 below. However, any method for characterizing a phytase activity, either by measuring the decrease in the amount of substrate or by measuring the accumulation of the products derived from the enzyme reaction, may be used to measure the phytase activity of the bacterial extract according to the invention.

The bacterial extract according to the invention is characterized in that it originates from a bacterium of the *Acidocella* genus. The characteristics of the bacteria included in the *Acidocella* genus are described in Kishimoto et al. (1995, System. Appl. Microbiol. 18, 85-91).

Preferably, the bacterial extract according to the invention expresses a phytase activity for which the optimum pH for activity is less than or equal to 4. The optimum pH for activity corresponds to the pH at which the phytase activity measured in the bacterial extract according to the invention is maxima.

According to a particular embodiment of the invention, the bacterial extract comprises a phytase activity having the following properties:

(a) optimum temperature=65° C.
(b) optimum pH=3.5

According to another particular embodiment of the invention, the bacterial extract comprises a phytase activity having the following properties:
(a) optimum temperature=70° C.
(b) optimum pH=4

According to another particular embodiment of the invention, the bacterial extract comprises a phytase activity having the following properties:
(a) optimum temperature=60° C.
(b) optimum pH=3.5

The terms "optimum temperature" and "optimum pH" are intended to mean the temperature and the pH at which the phytase activity measured in the bacterial extract according to the invention is maximal.

According to a particular embodiment of the invention, the bacterial extract according to the invention originates from a bacterial strain of the species *Acidocella aminolytica*, in particular the strain *A. aminolytica* ATCC 51361 or from a bacterial strain of the species *Acidocella facilis*, in particular the strain *A. facilis* ATCC 35904.

The present invention also relates to a method for preparing said bacterial extract. This method is characterized in that it comprises the steps of:
(a) culturing a bacterial strain of the *Acidocella* genus
(b) concentrating the bacteria cultured in step (a)
(c) grinding the bacteria isolated in step (b)
(d) centrifuging the ground material obtained in step (c)
(e) recovering the supernatant having the phytase activity derived from step (d).

According to the present method, a bacterial strain of the *Acidocella* genus is cultured in a suitable culture medium which allows the bacteria to multiply, and the pH of which is adjusted to the pH conditions of the natural environment in which said bacterial strain develops. Many culture media for bacteria are described in the literature, and those skilled in the art will be able to select them and adjust the pH conditions thereof. By way of example, a culture medium for acidophilic bacteria, in particular of the *Acidocella* genus, is described in Kishimoto et al., 1995, System. Appl. Microbiol. 18, 85-91).

After culturing, the bacteria obtained are concentrated. The bacteria can be concentrated by many means, in particular by centrifugation or by filtration. After concentration, the bacteria are ground. The grinding of the bacteria consists in rupturing the bacterial cells. It may be carried out by various means known to those skilled in the art. Preferably, the grinding is carried out by exposing the bacteria to an ultrasound field. The ground bacterial material is then centrifuged in order to separate the insoluble cell debris, and then to recover the centrifugation supernatant comprising the soluble cellular elements, and in particular enzymes expressing a phytase activity.

According to a particular embodiment of the invention, the bacterial strain used in the method according to the invention is a bacterial strain of the species *Acidocella aminolytica*, in particular the strain *A. aminolytica* ATCC 51361, or a bacterial strain of the species *Acidocella facilis*, in particular the strain *A. facilis* ATC 35904.

The present invention also relates to a method for producing the phytase according to the invention. According to one embodiment of the invention, this method is characterized in that it comprises the steps of:
(a) culturing a bacterial strain of the *Acidocella* genus
(b) concentrating the bacteria cultured in step (a)
(c) grinding the bacteria isolated in step (b)
(d) centrifuging the ground material obtained in step (c)
(e) recovering the supernatant having the phytase activity derived from step (d)
(f) purifying the phytase from the supernatant recovered in step (e).

Steps (a) to (e) of this method are common with steps (a) to (e) of the method for preparing a bacterial extract described above. Step (f) of the present method for preparing a phytase according to the invention consists in purifying the phytase from the supernatant recovered in step (e). The purification of the phytase may be carried out by any protein separation technique, in particular the electrophoresis and chromatography techniques well known to those skilled in the art. In order to achieve a purified phytase, those skilled in the art will be able to use the method for measuring the phytase activity mentioned above, in order to identify the purification fraction(s) containing said phytase.

Preferably, the bacterial strain used in the method according to the invention is a bacterial strain of the species *Acidocella aminolytica*, in particular the strain *A. aminolytica* ATCC 51361, or a bacterial strain of the species *Acidocella facilis*, in particular the strain *A. facilis* ATCC 35904.

According to another embodiment of the invention, in particular when the phytase according to the invention is secreted into the culture medium, this method is characterized in that it comprises the steps of:
(a) culturing a bacterial strain of the *Acidocella* genus
(b) recovering the culture medium by removing the bacteria
(c) purifying the phytase from the culture medium recovered in step (b).

According to this method, the step of recovering the culture medium by removing the bacteria can be carried out by any means of separating solid fractions included in the liquid fraction. In particular, filtration and centrifugation are suitable means for carrying out this step.

According to another embodiment of the invention, the method for producing the phytase according to the invention uses a transformed host organism according to the invention, and is characterized in that it comprises the steps of:
(a) culturing a transformed host organism according to the invention
(b) concentrating the transformed host organism cultured in step (a)
(c) grinding the transformed host organism isolated in step (b)
(d) centrifuging the ground material obtained in step (c)
(e) recovering the supernatant having the phytase activity derived from step (d)
(f) purifying the phytase from the supernatant recovered in step (e).

Step (f) of the present method for producing the phytase according to this embodiment of the invention consists in purifying the phytase from the supernatant recovered in step (e). The purification of the phytase may be carried out by any protein separation technique, in particular the electrophoresis and chromatography techniques well known to those skilled in the art. In order to achieve a purified phytase, those skilled in the art will be able to use the method for measuring the phytase activity mentioned above, in order to identify the purification fraction(s) containing said phytase.

Preferably, the transformed host organism used in this method is a microorganism. In particular, said microorganism may be a fungus, for example of the *Penicillium, Aspergillus, Chrysosporium* or *Trichoderma* genus, a bacterium, for example of the *Escherichia* genus, in particular *E. coli*, of the *Corynebacterium* genus or of the *Streptomyces* genus, a yeast, in particular of the *Saccharomyces, Kluyveromyces* or *Pichia* genus, a baculovirus or plant cells.

According to another embodiment of the invention, in particular when the phytase according to the invention is secreted into a culture medium, this method is characterized in that it comprises the steps of:
  (a) culturing a transformed host organism according to the invention
  (b) recovering the culture medium by removing said transformed host organism
  (c) purifying the phytase from the culture medium recovered in step (b).

According to this method, the step of recovering the culture medium by removing the transformed host organism may be carried out by any means of separating solid fractions included in a liquid fraction. In particular, filtration and centrifugation are means suitable for carrying out this step.

The present invention also relates to enzymatic compositions comprising at least [lacuna] phytase according to the invention. According to a particular embodiment, the enzymatic composition according to the invention comprises a bacterial extract according to the invention.

The term "enzymatic composition" is intended to mean a composition comprising at least [lacuna] phytase according to the invention, which phytase is combined with diverse adjuvants which promote its stability and its conservation. The enzymatic composition according to the invention may be in liquid form, said composition and the phytase which it contains then being in an aqueous solution, or in solid form, said composition and the phytase which it contains then being lyophilized in the form of a powder.

According to a particular embodiment of the invention, the enzymatic composition comprises, in addition to the phytase according to the invention, at least one additional enzyme. This additional enzyme may either have phytase activity, or have an activity other than phytase activity. When this additional enzyme has phytase activity, said phytase activity is preferably different from and complementary to the phytase activity of the phytase according to the invention. When this additional enzyme has an activity other than phytase activity, it may, for example, have xylanase, cellulase, β-glucanase, ferulic acid esterase, pullulanase, amidase, phosphatase or mannanase activity.

Preferably, said enzymatic compositions are intended to be incorporated into feedstuffs for livestock animals, in particular monogastric animals, preferably pigs or poultry.

The present invention also relates to a feed composition comprising at least [lacuna] phytase according to the invention.

The term "feed composition" is essentially intended to mean a feedstuff intended for livestock animals, in particular for the monogastric animals, preferably pigs or poultry. A feed composition according to the invention is ideally a feedstuff intended for livestock animals, supplemented with an enzymatic composition according to the invention. The feed composition according to the invention is therefore a feedstuff for livestock animals, to which at least one enzymatic composition according to the invention is added, said feedstuff and said enzymatic composition being mixed so as to obtain said feed composition.

According to a particular embodiment of the invention, said feed compositions comprise at least one transformed host organism according to the invention. According to another particular embodiment of the invention, said feed compositions comprise at least one bacterium of the *Acidocella* genus. Preferentially, the bacterium of the *Acidocella* genus is a bacterium of the species *Acidocella aminolytica*, in particular the strain *A. aminolytica* ATCC 51361, or a bacterium of the species *Acidocella facilis*, in particular the strain *A. facilis* ATCC 35904.

The invention also relates to feed compositions comprising at least one bacterial extract or a phytase according to the invention.

Advantageously, the feed compositions according to the invention are intended to be used in monogastric animal nutritions. According to a particular embodiment of the invention, said feed compositions are intended for pig nutrition. According to another particular embodiment of the invention, said feed compositions are intended for poultry nutrition.

The object of the present invention is also a method for producing a feed composition as described above.

According to a particular embodiment of the invention, said method consists in culturing a host organism according to the invention or a bacterium of the *Acidocella* genus, in concentrating said host organisms or said bacteria by any method of concentration known to those skilled in the art, in particular filtration or centrifugation, and then in incorporating said host organisms of said bacteria which have been concentrated, into a feed composition. Preferentially, when the method according to the invention uses a bacterium of the *Acidocella* genus, it is a bacterium of the species *Acidocella aminolytica*, in particular the strain *A. aminolytica* ATCC 51361, or a bacterium of the species *Acidocella facilis*, in particular the strain *A. facilis* ATCC 35904.

According to another particular embodiment of the invention, said method consists in isolating a bacterial extract according to the invention using the method for preparing said extract as described above, and then in incorporating the supernatant produced in step (e) of said method into a feed composition.

According to another particular embodiment of the invention, said method consists in producing a phytase according to the invention using one of the methods for producing said phytase as described above, and then in incorporating said phytase produced into a feed composition.

The present invention also relates to a method for increasing the assimilation of the inorganic phosphate contained in the phytase of plant-based feedstuffs by monogastric animals, characterized in that a phytase or an enzymatic composition according to the invention is incorporated into the nutrition of said animals. Preferably, said method is characterized in that said monogastric animals are fed with a feed composition according to the invention.

The invention also relates to a method for decreasing the addition of phosphorus to monograstric animal nutrition, characterized in that said animals are fed with a feed composition according to the invention.

The invention also relates to a method for decreasing the phosphorus waste derived from monogastric animal nutrition, characterized in that said animals are fed with a feed composition according to the invention.

The examples below make it possible to illustrate the present invention without, however, limiting the scope thereof.

EXAMPLE 1

Culturing of Bacteria of the *Acidocella* Genus

Bacteria of the *Acidocella* genus are Gram-negative acidophilic bacteria which develop in media at acid pH. By way of example, bacteria of the strains *A. aminolytica* ATCC 51361 and *A. facilis* ATCC 35904 can be used to implement the present invention. These bacteria can be cultured according to a similar method. In particular, they are cultured under aerobic conditions at 30° C. and pH 4 in medium composed of peptone and glucose. A standard culture medium is, for example, described in Kishimoto and Tano (1987, J. Gen. Appl. Microbiol. 33, 11-25). The medium used to express the phytase is free of inorganic phosphate and supplemented with phytate (0.4%) and with $CaCl_2$ (2.2 g/l).

EXAMPLE 2

Measurement of the Phytase Activity

The phytase activity is measured in liquid medium. It is carried out on samples of bacterial culture or on bacterial extracts according to the invention, or on phytases according to the invention. It is based on the method of Shimizu (1992, Biosci. Biotech. Biochem. 56(8), 1266-1269). The principle of this method consists in measuring the amount of inorganic phosphate released during the enzymatic reaction of the phytase with its substrate (1% sodium phytate solution). The amount of inorganic phosphate released is measured by reaction thereof with a chromogenic reagent (1 volume of 10.8% iron sulfate mixed extemporaneously with 4 volumes of 0.012M ammonium molybdate $H_2SO_4$). This reaction leads, in highly acidic medium, to the formation of a colored phosphomolybdate complex (in the presence of $Fe^{2+}$), and the amount of complex formed is quantified by measuring, on a spectrophotometer, the absorbance at 700 nm of the colored solution generated.

Two different reactions make it possible to measure the activity: a first measurement is carried out at the time the sample is brought into contact with the substrate (time T0) and a second after incubation for 60 min (time T60). The variation in absorbance between times T0 and T60 (versus the respective blanks consisting of buffer in place of the sample) is proportional to the amount of inorganic phosphate released during the enzymatic reaction.

A reference standard range is prepared by mixing 250 µl of $KH_2PO_4$ solution at the concentrations of 0.1 mM, 0.5 mM, 1 mM, 2 mM and 4 mM in the desired buffer with 250 µl of TCA and revealing with 450 µl of chromogenic reagent. One enzymatic unit is defined as the amount of enzyme which releases one micromole of inorganic phosphate per minute (at a given temperature and pH).

EXAMPLE 3

Isolation of a Bacterial Extract Containing a Phytase Activity

After culturing, the bacteria of the *Acidocella* genus are concentrated by centrifugation for 15 min at 5000 g and 4° C. The supernatant is removed and the bacteria thus concentrated are then resuspended in a formate (100 mM)-$CaCl_2$ (1 mM) buffer at pH 3.5, so as to concentrate them approximately 100-fold relative to their initial concentration in the culture medium. The concentrated bacteria are then ground using a "cell disrupter" (Cell-d) device used at a rate of two passes in a stream with a pressure of 2.5 kbar. The bacterial ground material is then centrifuged for 15 min at 5000 g and 4° C., and the supernatant, constituting the bacterial extract, is recovered and its phytase activity is measured.

EXAMPLE 4

Figure 3:
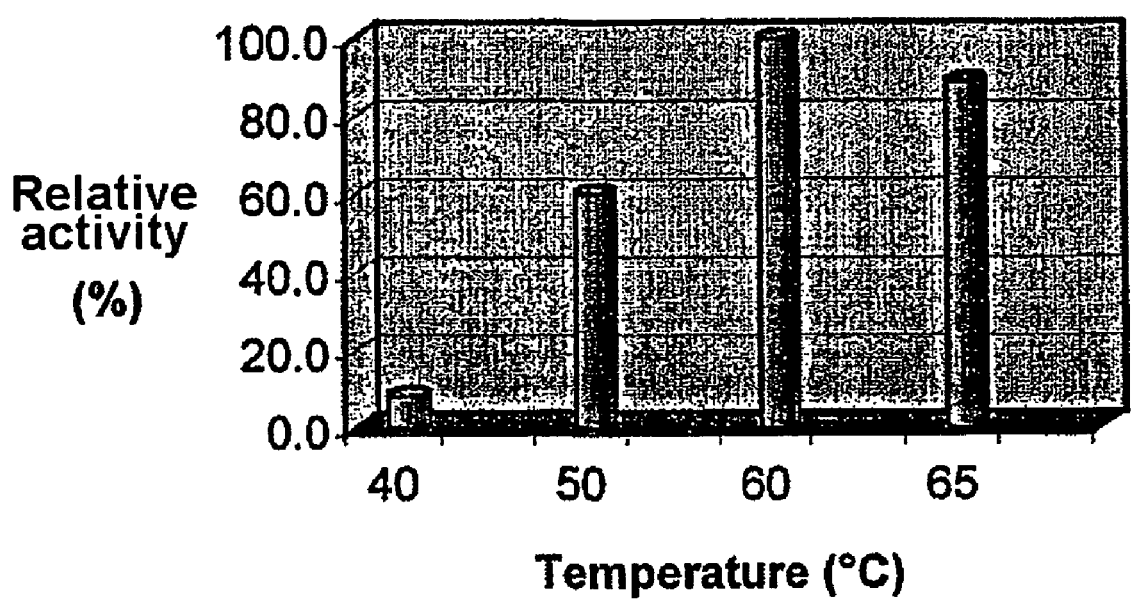
FIG. 3: Activity of the phytase of *Acidocella facilis* ATCC 35904 as a function of temperature. The value 100% of relative activity corresponds to the optimum activity of the phytase for a given temperature.

Characteristics of the Isolated Phytases According to the Invention 4.1. Phytase Activity as a Function of Temperature The activity of the phytases according to the invention was determined at various temperatures. The results of these measurements are given for the bacteria *Acidocella aminolytica* ATCC 51361 (FIG. 1) and *Acidocella facilis* ATCC 35904 (FIG. 3). The optimum temperatures for activity are 70° C. and 60° C., respectively, for the bacteria *Acidocella aminolytica* ATCC 51361 and *Acidocella facilis* ATCC 35904.

4.2. Phytase Activity as a Function of pH

Figure 2:
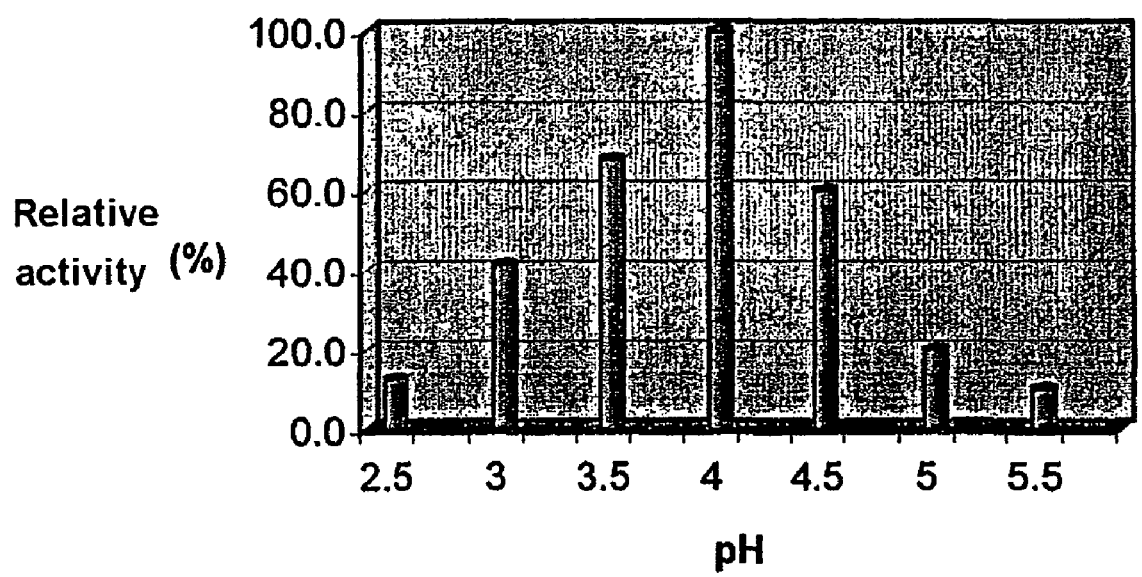
FIG. 2: Activity of the phytase of *Acidocella aminolytica* ATCC 51361 as a function of pH. The value 100% of relative activity corresponds to the optimum activity of the phytase for a given pH.
Figure 4:
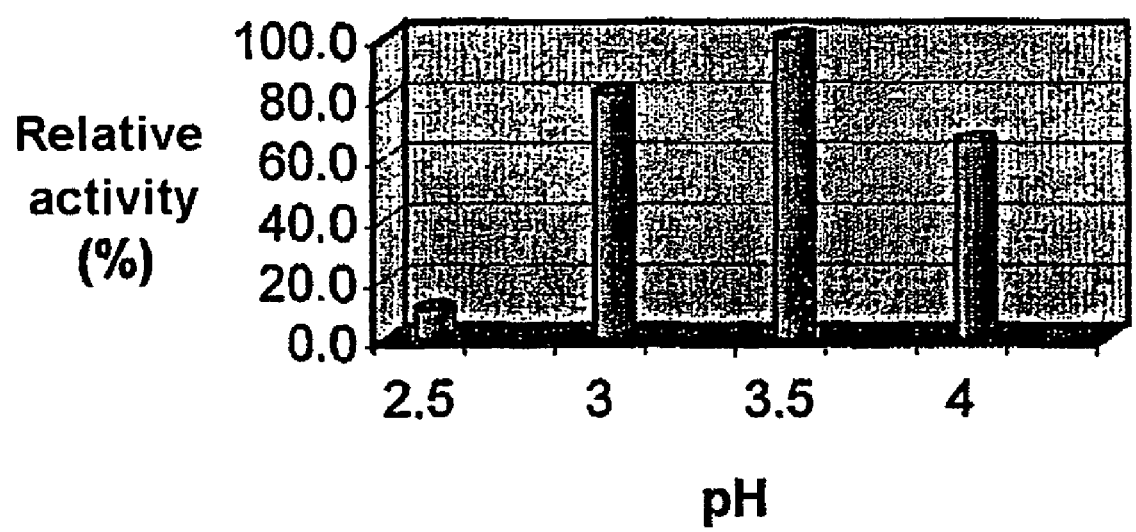
FIG. 4: Activity of the phytase of *Acidocella facilis* ATCC 35904 as a function of pH. The value 100% of relative activity corresponds to the optimum activity of the phytase for a given pH.

The activity of the phytases according to the invention was determined at various pHs. The results of these measurements are given for the bacteria *Acidocella aminolytica* ATCC 51361 (FIG. 2) and *Acidocella facilis* ATCC 35904 (FIG. 4). The optimum pHs for activity are 4 and 3.5, respectively, for the bacteria *Acidocella aminolytica* ATCC 51361 and *Acidocella facilis* ATCC 35904.

EXAMPLE 5

Purification of a Phytase According to the Invention 5.1. Preparation of the Crude Extract The cells of a bacterial strain of the *Acidocella* genus are centrifuged and then washed 3 times in MES buffer (25 mM), pH 6.5, containing 1 mM $CaCl_2$ in order to remove the phytate from the medium and the inorganic phosphate (accumulated during growth). The cell suspension thus obtained is then ruptured in a "cell disrupter" (1.5 kbar), and the pH is then lowered to 5.5 (by adding 3.7% hydrochloric acid).

The extract thus obtained is centrifuged at 20,000 g for 1 hour. The supernatant is then filtered through a membrane with a 0.45 µm porosity.

5.2. Anion Exchange Chromatography

The supernatant is passed over a column of the POROS 20 HQ type (4.6/100 mm: 1.7 ml of gel). The elution is carried out with an MES buffer (25 mM), pH 5.5, containing 1 mM $CaCl_2$ and 1M NaCl.

The phytase activity (50% of the activity injected) is found in the dead volume fraction.

5.3. Hydrophobic Interaction Chromatography

The fraction recovered at the end of anion exchange chromatography is brought to 1.5 M $(NH_4)_2SO_4$. This solution is then loaded onto a column of the POROS 20 HP2 type (HQ 4.6/100 mm: 1.7 ml of gel) pre-equilibrated with an MES buffer (25 mM), pH 5.5, containing 1 mM $CaCl_2$ and 1.5 M $(NH_4)_2SO_4$. The proteins are then eluted with a gradient of 1.5 to 0 M $(NH_4)_2SO_4$ in 20 column volumes.

The phytase activity is eluted at 0.95 M $(NH_4)_2SO_4$ in 3 fractions of 2 ml. These fractions are pooled and then dialyzed against 5 liters of MES buffer (20 mM), pH 5.5, containing 1 mM $CaCl_2$, at 4° C. overnight.

5.4. Cation Exchange Chromatography

The dialyzed solution is injected onto a column of the POROS 20 HS type (4.6/100 mm: 1.7 ml of gel) pre-equilibrated with an MES buffer (20 mM), pH 5.5, containing 1 mM $CaCl_2$. The proteins are eluted with a 0 to 1 M NaCl gradient in 20 column volumes.

The protein with phytase activity is eluted at an NaCl concentration of 0.35 M.

5.5. Gel Filtration

The fractions obtained in the preceding step are pooled, concentrated and loaded onto a SUPEROSE 12 hr 10/30 column (24 ml PHARMACIA®) pre-equilibrated with MES buffer (25 mM), pH 5.5, containing 1 M $CaCl_2$ and 0.1 M NaCl. The proteins were eluted with 24 ml of the buffer at a flow rate of 0.5 ml/min. 0.5 ml fractions were collected. The phytase activity is detected in three fractions between 14 and 15 ml of elution buffer (Table 1).

TABLE 1

Activity in the fractions of interest after the gel filtration step

| Fractions | Fluorescence Test "MUFp" (RFU/min) |
|---|---|
| 1 | 0 |
| 2 | 2240 |
| 3 | 2690 |
| 4 | 1134 |
| 5 | 0 |

The three fractions which exhibit a phytase activity were concentrated and loaded onto a 14.4% gel for SDS-PAGE. This gel reveals a main band of approximately 63 kDa.

EXAMPLE 6

Microsequencing of Internal Peptides

The band of interest (approximately 63 kDa) was cut out directly from the polyacrylamide gel. The dye contained in the gel was partially removed by 2 washes in 50% acetonitrile/50 mM Tris-HCl, pH 8.6. The protein, in polyacrylamide gel, was digested in 400 μl of 50 mM Tris-HCl buffer, pH 8.6/0.03% of SDS at 35° C. for 18 hours in the presence of 0.4 μg of endolysin-C (sequencing group, from Roche).

The peptides obtained were separated by HPLC on a DEAE-C18 on-line column 2.1 mm in diameter. The separating gradient was a gradient of 2 to 45% of acetonitrile/0.1% TFA.

Four peptides were purified, and then sequenced by the Edman method using an Applied Biosystems 473A sequencer.

TABLE 2

Sequences of the internal peptides obtained

| Peptides | Sequence |
|---|---|
| Peptide 1 | KVINFLMRQPDWK (SEQ ID NO: 12) |
| Peptide 2 | KNTAIIITYDDSDGGY (SEQ ID NO: 13) |
| Peptide 3 | KHLVIIYGENVSFDHY (SEQ ID NO: 14) |
| Peptide 4 | KMEGQNIGDLLNAK (SEQ ID NO: 15) |

EXAMPLE 7

Cloning of the Gene Encoding the Phytase 7.1. Definition of a Probe

On the basis of the sequences of the internal peptides, several degenerate oligonucleotides were synthesized in order to amplify a fragment of the gene of interest by PCR.

```
Oligo10      ATDATDATNGCNGTRTTYTT
SEQ ID
NO: 3):

Oligo12:     TCRTCRTASGTGATGATGATSGCSGTRTTYTT
SEQ ID
NO: 4):

Oligo22:     AARATGGARGGNCARAAYATHGG
SEQ ID
NO: 5):

Oligo23:     ATGGAAGGCCAGAAYATCGGCGA
SEQ ID
NO: 6):

Oligo25:     ATCGGCGAYCTBCTBAAYGCCAA
SEQ ID
NO: 7):
```

Combinations of the primers Oligo10 and Oligo12 with the three primers Oligo 22, 23 and 25 were tested, and the pair of primers Oligo12 and Oligo22 made it possible to isolate the 500 bp fragment from the genomic DNA of a strain of the *Acidocella* genus. After purification, this DNA fragment was sequenced.

Analysis of this sequence made it possible to demonstrate, in this fragment, a nucleic acid sequence encoding peptide 1, suggesting that the sequenceed PCR product effectively corresponds to the protein of interest which was the subject of the microsequencing.

On the basis of the sequence obtained from the PCR product of approximately 500 bp, further primers, Oligo29 and Oligo30, were defined in order to have a set of nondegenerate primers specific to the gene of interest.

Oligo29(SEQ ID NO: 8): TTCATGGGTGGCTTCGATC

Oligo30(SEQ ID NO: 9): GCTGCCGCATCAG-GAAGTTG 7.2. Southern Blotting

The PCR product of approximately 500 bp obtained by amplification with the primers Oligo12 and Oligo22 was used as a probe in Southern blotting experiments.

In order to label the probe, 10 mg of purified PCR product were labeled by random priming using the Q-BIOgene labeling kit.

10 μg of genomic DNA were digested, respectively, with Eco RI, Sac II or Bam HI, and then loaded onto a 1% agarose gel. After migration, the DNA was transferred by capillarity onto a nylon membrane (BIODYNE® Plus membrane, Pall Gelman).

A prehybridization was carried out for 4 h at 60° C. with a buffer of 5×SSC, 5× Denhardt's, 1% SDS and 100 μg/ml of denatured fish DNA.

The hybridization was then carried out for 16 h at 60° C. with a buffer containing 10 ml of prehybridization buffer and 10 ng of the probe at $4.08 \times 10^8$ cpm/μg (counting on a dry scintillation counter, i.e. in the absence of scintillant).

Several washing phases were then followed:
2 washes: 2×SCC+0.1% SDS for 3 min at 20° C.
2 washes: 0.5×SCC+0.1% SDS for 3 min at 20° C.
2 washes: 0.4×SCC+0.1% SDS for 15 min at 50° C.
The gel was revealed on film after exposure for 24 h at −80° C.

These experiments made it possible to show that Sac II cleaves in the portion of the gene used as a probe, but there is no Eco RI or Bam HI site in this sequence. The Eco RI and Bam HI digestions release, respectively, a fragment of approximately 4 kb and a fragment larger than 9 kb, to which the target sequence hybridizes.

Since it was known, based on biochemical studies, that the protein of interest should be encoded by a gene of approximately 1.6 kb, a genomic DNA library, with complete Eco RI digestion, was constructed.

7.3. Construction of a Genomic Library

Approximately 30 µg of genomic DNA of a strain of the *Acidocella* genus were digested with Eco RI. After migration on a 0.7% agarose gel, the fragments of between 3 and 4 kb in size were purified using the QIAEX II gel extraction kit (Qiagen) and desalified (microbio spin 6, Biorad). The fragments of between 2.5 and 3 kb in size and also those of between 4 and 5 kb in size were also purified.

The purified fragments were inserted into a vector pBlueScript KS (II+) using T4 DNA ligase (QBIOgene)

The products of the ligation carried out with the fragments of between 3 and 4 kb in size were used to transform the *E. coli* strain MC 1061 by electroporation. After transformation, the cells were taken up in SOC (2% tryptone, 0.5% yeast extract, 0.05% NaCl, 2.5 mM KCl, 10 mM $MgCl_2$, 20 mM glucose) and placed at 37° C. for 1 hour, before being bloated out on an LB medium supplemented with ampicillin (100 µg/ml). The Petri dishes were then incubated overnight at 37° C.

7.4. Screening of the Genomic Library 383 different colonies were then screened by PCR using the set of primers Oligo29 and Oligo30.

Among these clones, 4 made it possible to obtain a pCR product of approximately 400 bp. Two of the clones allowing amplification of a fragment of expected size were used to prepare a plasmid mini-preparation (using the Qiagen kit).

7.5. Sequencing of the Genomic Inserts

The two plasmids identified were digested with Eco RI and Eco RV. Sequencing of their inserts showed that these two plasmids carried the same insert. Analysis of the sequences made it possible to demonstrate an open reading frame of 1665 pb corresponding to a protein of 554 amino acids. In addition, the sequences encoding the 4 internal peptides sequenced in Example 6 were found in this reading frame.

EXAMPLE 8

Subcloning of the Identified Gene

The sequence containing the open reading frame (called ORF281) identified in the genomic insert cloned in Example 7 was amplified by PCR with the oligonucleotides 5'ORF281 (SEQ ID NO: 10) and 3'ORF281 (SEQ ID NO: 11).

```
5'ORF281    5'TAA CGA TAA CAT ATG AAT ATC CGC CGG
            GCT CT 3'

3'ORF281    5'ATA TCT GAT AAG CTT TTA TTC GGC GTG
            CGC GGC 3'
```

The PCR product was purified and digested with the Nde I and Hind III restriction enzymes, and then subcloned into the vector pETCm digested with the same enzymes. The vector obtained is called pETCm281. The ORF281 insert was sequenced in order to verify that the sequence cloned is identical to that determined from the genomic inserts previously cloned.

The vector pETCm comprises a chloramphenicol resistance gene. Its use, and therefore that of chloramphenicol resistance as a selection marker, allows in vivo expression in a kanamycin-resistant strain of *E. coli*: the strain BL21 appA (phytase−).

EXAMPLE 9

Expression of the Gene Subcloned in *E. Coli*

9.1. Preparation of the Recombinant *E. Coli* Strains

In vivo expression assays were carried out in the *E. coli* strain BL21 appA. This strain no longer expresses endogenous phytase due to an insertion of a kanamycin resistance gene in the appA gene encoding the *E. coli* phytase. A control vector was also prepared with the TEM gene encoding *E. coli* β-lactamase. The TEM gene was also cloned in the vector pETCm, and the vector obtained was called pETCmTEM.

The *E. coli* strain BL21 appA was transformed with the vectors pETCmTEM or pETCm281. Isolated colonies were selected on LB medium supplemented with 60 mg/L of kanamycin and with 20 mg/L of chloramphenicol, A colony of each type was cultured in LB medium supplemented with Kanamycin and with chloramphenicol at the same concentrations. These cultures were used to prepare glycerols (one volume of cells per volume of 40% glycerol), from which stocks the cultures intended for carrying out the expression assays are seeded. These glycerol stocks are stored at −80° C.

9.2. Expression Assays

The *E. coli* strain BL21 appA pETCm281 was cultured in M98 medium (modified Terrific Broth medium (modified with glucose) containing, per liter, 12 g of bactotryptone, 24 g of yeast extract, 9.4 g of $K_2HPO_4$ and 2.2 g of $KH_2PO_4$, pH 7.2, autoclaved, to which 20 mL of glucose (50%) per liter of medium are added before use) in parallel with the *E. coli* strain BL21 appA pETCmTEM. The expression is induced by adding 0.25 mM of IPTG, and carried out at two temperatures: 30 and 37° C.

After induction for 3 hours, the cultures are centrifuged. The phytase activity is assayed on each pellet resuspended in formate buffer to achieve a final concentration of 5 mg/mL of dry cells. No activity was found for the strain containing pETCm281 nor for the strain containing pETCmTEM, whatever the culturing conditions.

Aliquots of the induced and noninduced cultures containing pETCm281 were then treated with ultrasound and then centrifuged. The supernatant represented the soluble protein fraction and the pellet represented the insoluble proteins. These two fractions were loaded onto a denaturing SDS-PAGE gel.

A protein band of MW 63 kDa is clearly apparent in the insoluble fraction of the *E. coli* strain BL21 appA pETCm281 induced with IPTG. No corresponding band is found in the noninduced negative control. ORF281 is therefore clearly expressed in *E. coli*. However, the corresponding protein is insoluble and probably inactive in this form.

9.3. Solubilization and Renaturation of the Inclusion Bodies

A series of steps aimed at solubilizing and renaturing the protein encoded by ORF281 were carried out in order to determine whether or not this protein has a phytase activity.

The *E. coli* strain BL21 appA pETCm281 is cultured in M98 medium and then induced with 0.25 mM of IPTG when the OD at 600 nm reaches 0.4. After induction for 3 hours, the culture is centrifuged (final OD in the region of 1). The pellet is taken up in 20 mM Tris-HCl buffer, pH 8.0, in a proportion of 4 mL per 100 mL of culture. The cells are treated with ultrasound at 4° C.: 4 cycles of 10 seconds at a power of 500 Watts. The $OD_{600}$ decreases from 14 to 3. The suspension is then centrifuged for 10 minutes at 16,000 g, and the supernatant is then removed.

The pellet is resuspended in 5 ml, per 100 ml of culture, of solubilization buffer: 20 mM Tris-HCl, pH 8, 8M urea, 0.5 M NaCl, 1 mM 2-mercaptoethanol. The suspension is treated with ultrasound at a rate of 4 cycles of 10 seconds at a power of 500 Watts, and then stirred for 1 hour at ambient temperature. 30 ml of this suspension are then dialyzed at 4° C. for 16 hours against 3 liters of 25 mM MES renaturation buffer, pH 6.5, containing 0.5 M NaCl and 1 mM mercaptoethanol (Cut-off 10 kDa). A second dialysis is carried out against 3 liters of 25 mM MES renaturation buffer, pH 5.5, containing 0.5 M NaCl and 1 mM mercaptoethanol (Cutt-off 10 kDa), for 5 hours. The suspension is then centrifuged for 10 minutes at 16,000 g and then stored at 4° C. before being assayed enzymatically.

The same culturing, solubilization and renaturation protocol was applied to the *E. coli* strain BL21 appA pETCmTEM.

9.4. Activity of the Inclusion Bodies

The suspensions of the renatured proteins produced by the *E. coli* strains BL21 appA pETCm281 and pETCmTEM were concentrated 10-fold on Nanosep™ 10K Omega (Pall). The phytase activity is measured on these concentrated solutions according to a standard protocol (at pH 3.5). This assay was carried out in duplicate.

|  | Activity mU/ml |
|---|---|
| *E. coli* BL21 appA pET-TEM. Assay 1 | 0 |
| *E. coli* BL21 appA pET-TEM. Assay 2 | 0 |
| *E. coli* BL21 appA pET281. Assay 1 | 100 |
| *E. coil* BL21 appA pET281. Assay 2 | 100 |

A phytase activity is detected only in the *E. coli* strain BL21 appA pETCm281. This activity is confirmed using a PMUF assay. Using this fluorometric method, no activity is detected in the *E. coli* strain BL21 appA pETCmTEM, although this assay is five times more sensitive than the colorimetric method generally used.

9.5. Purification of the Inclusion Bodies

The resolubilized inclusion body fraction of the *E. coli* strain BL21 appA pETCm281 was loaded onto a POROS 20 HS column (4.6/100 mm: 1.7 ml of gel) pre-equilibrated with a 20 mM MES buffer, pH 5.5, containing 1 mM $CaCl_2$. The proteins are eluted with an NaCl gradient of 0 to 1 M in 20 column volumes.

The phytase activity is eluted at an NaCl concentration of 0.35 M. This result is identical in all respects to that obtained in Example 5.4. with the native phytase.

In parallel, a total extract (soluble and insoluble proteins) of *E. coli* strain BL21 appA pETCmTEM was loaded onto the same column and the proteins were eluted under the same conditions. No phytase activity could be detected in the fractions eluted between 0.15 and 0.45 M NaCl.

9.6. SDS-PAGE Gel

The fraction exhibiting a phytase activity, derived from the cation exchange column, was loaded onto an SDS-PAGE gel (10% acrylamide) after 10-fold concentration on NANOSEP™. A lysate of cells (induced with IPTG) of *E. coli* BL21 appA pETCm281 and *E. coli* BL21 appA pETCmTEM were also loaded onto the same gel.

It is again clearly apparent that only the *E. coli* BL21 appA pETCm281 lysate contains a band of MW 63 kDa. In the column-purified fraction exhibiting a phytase activity, a major band of MW 61-63 kDa is present.

These results therefore show, after subcloning in *E. coli* BL21 appA that ORF281 clearly encodes a phytase.

EXAMPLE 10

Characteristics of the Purified Recombinant Phytase

10.1. Phytase Activity as a Function of Temperature

Figure 5:
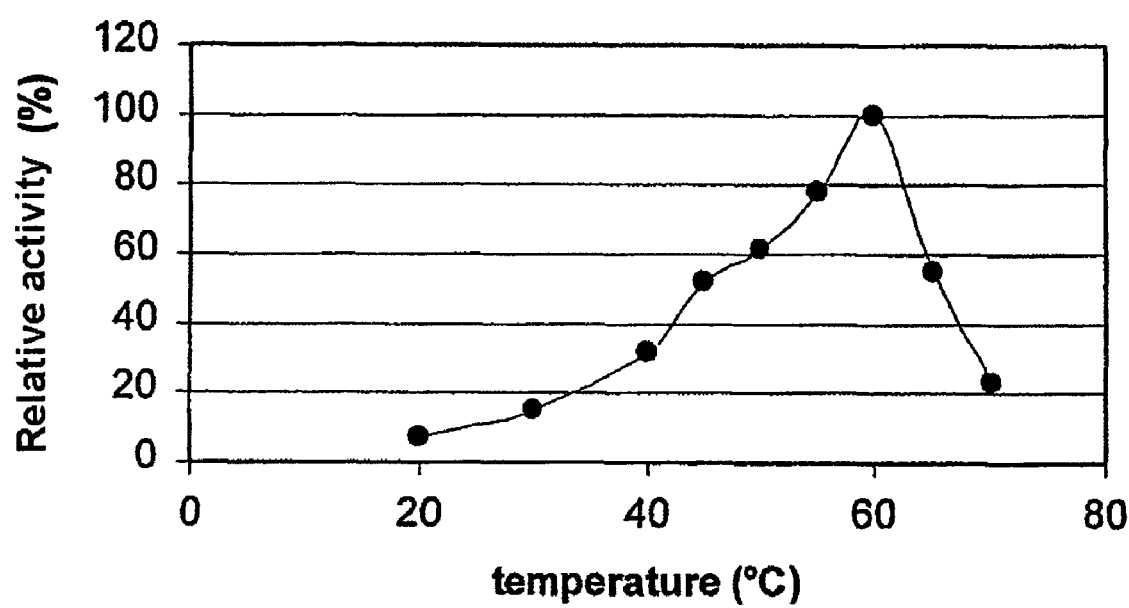
FIG. 5: Activity of the phytase contained in the fraction purified in Example 5.5 and encoded by ORF281, as a function of temperature. The value 100% of relative activity corresponds to the optimum activity of the phytase for a given temperature.
Figure 6:
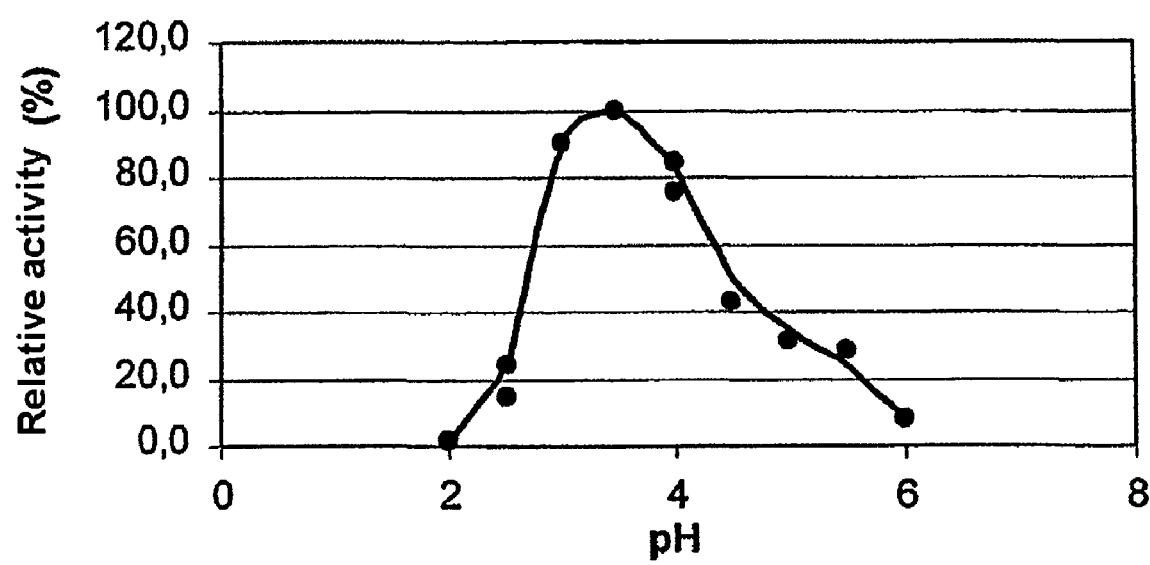
FIG. 6: Activity of the phytase contained in the fraction purified in Example 5.5 and encoded by ORF281, as a function of pH. The value 100% of relative activity corresponds to the optimum activity of the phytase for a given pH.

The activity of the phytase contained in the fraction purified in Example 5.5 and encoded by ORF281 was determined at various temperatures. The results of these measurements are given in FIG. 5. The optimum temperature for activity measured is 60° C. The assay was carried out at pH 3.

4.2. Phytase Activity as a Function of pH

The activity of the phytase contained in the fraction purified in Example 5.5 and encoded by ORF281 was also determined at various pHs. The results of these measurements are given in FIG. 5. The optimum pH activity is 3.5. The assay was carried out at 60° C., with the following succession of buffers: glycine-HCl (for pHs of 2 to 2.5), formate (pHs of 2.5 to 4), acetate (pHs of 4 to 5) and MES (pHs of 5 to 6).

EXAMPLE 11

Homologous Sequence Research

The sequence containing the open reading frame identified in the genomic fragment cloned in Example 7 was used as a probe to search for homologous sequences among microorganisms of the *Acidocella* and *Acidiphilium* genera.

The strains tested belong to the species *Acidocella aminolytica, Acidocella facilis, Acidiphilium angustrum,* and *Acidiphilium multivorum*.

10 ng of purified PCR product were labeled by random priming using the Q-BIOgene labeling kit. 10 μg of genomic DNA of the various strains to be tested were digested, respectively, with Eco RI or Eco RV and then loaded onto two 1% aragose gels. After migration, the DNA was transferred by capillarity onto two nylon membranes (BIODYNE® Plus membrane, Pall Gelman).

A prehybridization was carried out for 4 h at 60° C. with a buffer of 5×SSC, 5× Denhardt's, 1% SDS and 100 μg/ml of denatured fish DNA.

The hybridization was then carried out for 16 h at 60° C. with a buffer containing 10 ml of prehybridization buffer and 10 ng of the probe at respectively $7 \times 10^8$ and $9 \times 10^8$ cpm/μg for membrane 1 (EcoRI) and membrane 2 (EcoRV) (counting in a dry scintillation counter, i.e. in the absence of scintillant).

Several washing phases then followed:
2 washes: 2×SCC+0.1% SDS for 3 min at 20° C.
2 washes: 0.5×SCC+0.1% SDS for 3 min at 20° C.
2 washes: 0.4×SCC+0.1% SDS for 15 min at 50° C.

The membranes were revealed on film after exposure for 65 h at −80° C.

No significant difference was observed between the two autoradiographs.

The results show the presence, in all the strains of the *Acidocella* genus tested, of selective hybridization of the probe containing the open reading frame identified in Example 7. These results suggest that significant sequence homology exists between genes of the bacteria of the *Acidocella* genus and the identified open reading frame encoding a phytase. In addition, they strongly suggest that these genes also encode phytases.

On the other hand, no hybridization was obtained with the probe in microorganisms of the *Acidiphilium* genus. This observation is in agreement with the lack of detection of a phytase activity using microbiological methods in the microorganisms of this genus.

---

The invention claimed is:

1. An isolated polynucleotide selected from the group consisting of:
   (a) an isolated polynucleotide encoding a phytase consisting of the nucleotide sequence set forth in SEQ ID NO:1, and
   (b) an isolated polynucleotide consisting of the nucleotide sequence that is 100% complementary to the full-length sequence set forth in SEQ ID NO:1.

2. The polynucleotide as claimed in claim 1, wherein it originates from a bacterium of the *Acidocella* genus.

3. The polynucleotide as claimed in claim 2, wherein it encodes a phytase for which the optimum pH for activity is less than or equal to 4.

4. A chimeric gene comprising at least, functionally linked to one another:
   (a) a promoter which is functional in a host organism
   (b) a polynucleotide as claimed in claim 1
   (c) a terminator element which is functional in host organism.

5. The chimeric gene as claimed in claim 4, further comprising a signal peptide or a transit peptide which is functional in said host organism.

6. An expression or transformation vector containing a chimeric gene as claimed in claim 4.

7. The vector as claimed in claim 6, characterized in that it is a plasmid, a phage or a virus.

8. A transformed host organism containing a chimeric gene as claimed in claim 4.

9. The host organism as claimed in claim 8, characterized in that it is a microorganism.

10. The host organism as claimed in claim 9, characterized in that the microorganism is selected from bacteria, fungi, yeast and viruses.

11. The host organism as claimed in claim 10, characterized in that the microorganism is a bacterium selected from the *Corynebacterium*, *Streptomyces* and *Escherichia* genera.

12. The host organism as claimed in claim 10, characterized in that the microorganism is a fungus selected from the *Penicillium*, *Aspergillus*, *Chrysosporium* and *Trichoderma* genera.

13. The host organism as claimed in claim 10, characterized in that the microorganism is a yeast selected from the *Saccharomyces*, *Kluyveromyces* and *Pichia* genera.

14. The host organism as claimed in claim 8, characterized in that it is a plant cell, a plant or a part of a plant.

15. A method for producing a phytase, the method comprising:
   (a) culturing a transformed host organism containing a chimeric gene comprising at least, functionally linked to one another, a promoter that is functional in the host organism, an isolated polynucleotide according to claim 1, and a terminator element that is functional in the host organism,
   (b) concentrating the transformed host organism cultured in step (a),
   (c) grinding the transformed host organism insolated in step (b),
   (d) centrifuging the ground material obtained in step (c),
   (e) recovering the supernatant having the phytase activity derived from step (d), and
   (f) purifying the phytase from the supernatant recovered in step (e).

16. A method for producing a phytase, the method comprising:
   (a) culturing a transformed host organism containing a chimeric gene comprising at least, functionally linked to one another, a promoter that is functional in the host organism, an isolated polynucleotide according to claim 1, and a terminator element that is functional in the host organism,
   (b) recovering the culture medium by removing said transformed host organism, and
   (c) purifying the phytase from the culture medium recovered in step (b).

17. A feed composition comprising at least one transformed host organism containing a chimeric gene comprising at least, functionally linked to one another:
   (a) a promoter which is functional in a host organism,
   (b) an isolated polynucleotide according to claim 1, and
   (c) a terminator element that is functional in the host organism.

18. A feed composition, comprising at least one phytase encoded by an isolated polynucleotide according to claim 1.

19. A method for producing a feed composition, the method comprising:
   (a) culturing a host organism containing a chimeric gene comprising at least, functionally linked to one another, a promoter that is functional in the host organism, an isolated polynucleotide according to claim 1, and a terminator element that is functional in the host organism,
   (b) concentrating the host organism cultured in step (a), and
   (c) incorporating the host organism isolated in step (b) into said feed composition.

20. A method for producing a feed composition as claimed in claim 18, characterized in that it comprises the steps of:
   (a) culturing a bacterial strain of the *Acidocella* genus,
   (b) concentrating the bacteria cultured in step (a),
   (c) grinding the bacteria isolated in step (b),
   (d) centrifuging the ground material obtained in step (c),
   (e) recovering the supernatant having the phytase activity derived from step (d),
   (f) purifying the phytase from the supernatant recovered in step (e), and
   (g) incorporating the phytase purified in step (f) into said feed composition.

21. A method for producing a feed composition as claimed in claim 18, characterized in that it comprises the steps of:
   (a) culturing a bacterial strain of the *Acidocella* genus,
   (b) recovering the culture medium by removing the bacteria,
   (c) purifying the phytase from the culture medium recovered in step (b), and
   (d) incorporating the phytase purified in step (c) into said feed composition.

22. A method for producing a feed composition comprising at least one phytase, the method comprising:
  (a) culturing a transformed host organism containing a chimeric gene comprising at least, functionally linked to one another, a promoter that is functional in the host organism, an isolated polynucleotide according to claim 1, and a terminator element that is functional in the host organism,
  (b) concentrating the transformed host organism cultured in step (a),
  (c) grinding the transformed host organism isolated in step (b),
  (d) centrifuging the ground material obtained in step (c),
  (e) recovering the supernatant having the phytase activity derived from step (d),
  (f) purifying the phytase from the supernatant recovered in step (e), and
  (g) incorporating the phytase purified in step (f) into said feed composition.

23. A method for producing a feed composition comprising at least one phytase, the method comprising:
  (a) culturing a transformed host organism containing a chimeric gene comprising at least, functionally linked to one another, a promoter that is functional in the host organism, an isolated polynucleotide according to claim 1, and a terminator element that is functional in the host organism,
  (b) recovering the culture medium by removing said transformed host organism,
  (c) purifying the phytase from the culture medium recovered in step (b), and
  (d) incorporating the phytase purified in step (c) into said feed composition.

24. An isolated polynucleotide comprising a nucleotide sequence that exhibits at least 95% identity to the nucleotide sequence set forth in SEQ ID NO:1.

* * * * *